United States Patent
Shahana

(10) Patent No.: US 10,994,805 B2
(45) Date of Patent: May 4, 2021

(54) HUMAN-POWERED VEHICLE CONTROL DEVICE

(71) Applicant: Shimano Inc., Osaka (JP)

(72) Inventor: Satoshi Shahana, Osaka (JP)

(73) Assignee: Shimano Inc., Osaka (JP)

( * ) Notice: Subject to any disclaimer, the term of this patent is extended or adjusted under 35 U.S.C. 154(b) by 0 days.

(21) Appl. No.: 16/364,265

(22) Filed: Mar. 26, 2019

(65) Prior Publication Data

US 2019/0300114 A1  Oct. 3, 2019

(30) Foreign Application Priority Data

Mar. 29, 2018  (JP) .............................. JP2018-066079

(51) Int. Cl.
| | |
|---|---|
| *B62M 9/123* | (2010.01) |
| *B62M 25/08* | (2006.01) |
| *G01P 3/50* | (2006.01) |
| *G01P 1/02* | (2006.01) |
| *G01C 22/00* | (2006.01) |
| *B62J 45/20* | (2020.01) |
| *B62J 50/20* | (2020.01) |

(52) U.S. Cl.
CPC .............. *B62M 9/123* (2013.01); *B62J 45/20* (2020.02); *B62J 50/20* (2020.02); *B62M 25/08* (2013.01); *G01C 22/002* (2013.01); *G01P 1/02* (2013.01); *G01P 3/50* (2013.01)

(58) Field of Classification Search
CPC ........ B62M 9/123; B62M 25/08; B62M 6/45; B62J 45/20; B62J 50/20; G01P 3/50; G01P 1/02; G01P 3/487; G01C 22/002; A61B 5/0002; A61B 5/6895; A61B 5/024

See application file for complete search history.

(56) References Cited

U.S. PATENT DOCUMENTS

| | | | |
|---|---|---|---|
| 9,114,850 B2 * | 8/2015 | Tanaka | ................ B60L 15/2054 |
| 2013/0267376 A1 | 10/2013 | Takachi | |
| 2014/0222268 A1 * | 8/2014 | Tsuchizawa | ............ B60L 50/20 701/22 |

(Continued)

FOREIGN PATENT DOCUMENTS

| | | |
|---|---|---|
| JP | 9-207863 A | 8/1997 |
| JP | 11-180376 A | 7/1999 |

(Continued)

*Primary Examiner* — Justin Holmes
(74) *Attorney, Agent, or Firm* — Global IP Counselors, LLP

(57) ABSTRACT

A human-powered vehicle control device includes an electronic controller that controls a motor. The motor assists in propulsion of a human-powered vehicle including a transmission configured to change, in steps, a first ratio of a rotational speed of a drive wheel to a rotational speed of a rotary body to which human drive force is input. The controller controls the motor in a first control state if the first ratio is changed by only one step during a predetermined period or a signal is received for changing the first ratio by one step during the predetermined period. The controller controls the motor in a second control state that differs from the first control state if the first ratio is changed by at least two steps during the predetermined period or a signal is received for changing the first ratio by at least two steps during the predetermined period.

18 Claims, 8 Drawing Sheets

(56) References Cited

U.S. PATENT DOCUMENTS

2014/0235383 A1* 8/2014 Wesling .................. B62M 6/55
474/80
2015/0120119 A1 4/2015 Tauchi et al.

FOREIGN PATENT DOCUMENTS

| JP | 2000-118481 A | 4/2000 |
|---|---|---|
| JP | 2002-240772 A | 8/2002 |
| JP | 2012-121338 A | 6/2012 |
| JP | 2013-47085 A | 3/2013 |
| JP | 2013-216176 A | 10/2013 |
| JP | 5566975 B2 | 8/2014 |
| JP | 2015-110402 A | 6/2015 |

\* cited by examiner

HUMAN-POWERED VEHICLE CONTROL DEVICE

CROSS-REFERENCE TO RELATED APPLICATIONS

This application claims priority to Japanese Patent Application No. 2018-066079, filed on Mar. 29, 2018. The entire disclosure of Japanese Patent Application No. 2018-066079 is hereby incorporated herein by reference.

BACKGROUND

Technical Field

The present invention generally relates to a human-powered vehicle control device.

Background Information

Japanese Laid-Open Patent Publication No. 2013-47085 discloses an example of a human-powered vehicle control device configured to control a transmission that changes a transmission ratio of a human-powered vehicle and a motor that assists in propulsion of the human-powered vehicle.

SUMMARY

One object of the present disclosure is to provide a human-powered vehicle control device configured to suitably control a motor that assists in propulsion of a human-powered vehicle.

A human-powered vehicle control device in accordance with a first aspect of the present disclosure comprises an electronic controller that controls a motor. In the human-powered vehicle control device, the motor assists in propulsion of a human-powered vehicle including a transmission configured to change, in steps, a first ratio of a rotational speed of a drive wheel to a rotational speed of a rotary body to which human drive force is input. The electronic controller is configured to control the motor in a first control state in at least one of a case in which the first ratio is changed by only one step during a predetermined period and a case in which a signal is received for changing the first ratio by one step during the predetermined period. The electronic controller is configured to control the motor in a second control state that differs from the first control state in at least one of a case in which the first ratio is changed by at least two steps during the predetermined period and a case in which a signal is received for changing the first ratio by at least two steps during the predetermined period.

In accordance with the human-powered vehicle control device of the first aspect, the motor is controlled in a suitable manner for a case in which the first ratio is changed by one step and a case in which the first ratio is continuously changed by at least two steps.

In accordance with a second aspect of the present disclosure, the human-powered vehicle control device according to the first aspect is configured so that the electronic controller is configured to control the motor in accordance with the human drive force input to the human-powered vehicle. The electronic controller is configured to control the motor so that a second ratio of an assist force produced by the motor to the human drive force in the second control state is larger than the second ratio in the first control state.

In accordance with the human-powered vehicle control device of the second aspect, the motor is controlled so that the second ratio in the second control state is larger than the second ratio in the first control state.

In accordance with a third aspect of the present disclosure, the human-powered vehicle control device according to the second aspect is configured so that the second ratio is increased as the steps of the first ratio changed during the predetermined period increase in number or as the steps of the first ratio changed by the signal received during the predetermined period increase in number.

In accordance with the human-powered vehicle control device of the third aspect, the second ratio in the second control state is increased as the number of steps of the changed first ratio increases.

In accordance with a fourth aspect of the present disclosure, the human-powered vehicle control device according to the first aspect is configured so that the electronic controller is configured to control the motor in accordance with the human drive force input to the human-powered vehicle. The electronic controller is configured to control the motor so that a second ratio of an assist force produced by the motor to the human drive force in the second control state is smaller than the second ratio in the first control state.

In accordance with the human-powered vehicle control device of the fourth aspect, the motor is controlled so that the second ratio in the second control state is smaller than the second ratio in the first control state.

In accordance with a fifth aspect of the present disclosure, the human-powered vehicle control device according to the fourth aspect is configured so that the second ratio is decreased as the steps of the first ratio changed during the predetermined period increase in number or as the steps of the first ratio changed by the signal received during the predetermined period increase in number.

In accordance with the human-powered vehicle control device of the fifth aspect, the second ratio in the second control state is decreased as the number of steps of the changed first ratio increases.

In accordance with a sixth aspect of the present disclosure, the human-powered vehicle control device according to any one of the first to fifth aspects is configured so that the electronic controller is configured to control the motor in accordance with the human drive force input to the human-powered vehicle. The electronic controller is configured to control the motor so that a maximum value of an output of the motor is larger in the second control state than in the first control state.

In accordance with the human-powered vehicle control device of the sixth aspect, the motor is controlled so that the maximum value of the output of the motor in the second control state is larger than the maximum value of the output of the motor in the first control state.

In accordance with a seventh aspect of the present disclosure, the human-powered vehicle control device according to the sixth aspect is configured so that the maximum value is increased as the steps of the first ratio changed during the predetermined period increase in number or as the steps of the first ratio changed by the signal received during the predetermined period increase in number.

In accordance with the human-powered vehicle control device of the seventh aspect, the maximum value of the output of the motor in the second control state is increased as the number of steps of the changed first ratio increases.

In accordance with an eighth aspect of the present disclosure, the human-powered vehicle control device according to any one of the first to fifth aspects is configured so that the electronic controller is configured to control the motor in accordance with the human drive force input to the human-powered vehicle. The electronic controller is configured to control the motor so that a maximum value of an output of the motor is smaller in the second control state than in the first control state.

In accordance with the human-powered vehicle control device of the eighth aspect, the motor is controlled so that the maximum value of the output of the motor in the second control state is smaller than the maximum value of the output of the motor in the first control state.

In accordance with a ninth aspect of the present disclosure, the human-powered vehicle control device according to the eighth aspect is configured so that the maximum value is decreased as the steps of the first ratio changed during the predetermined period increase in number or as the steps of the first ratio changed by the signal received during the predetermined period increase in number.

In accordance with the human-powered vehicle control device of the ninth aspect, the maximum value of the output of the motor in the second control state is decreased as the number of steps of the changed first ratio increases.

In accordance with a tenth aspect of the present disclosure, the human-powered vehicle control device according to any one of the first to ninth aspects is configured so that the electronic controller is configured to control the motor in accordance with the human drive force input to the human-powered vehicle. The electronic controller is configured to control the motor so that a first response speed of an output of the motor in a case in which the human drive force is increased in the second control state is higher than the first response speed in the first control state.

In accordance with the human-powered vehicle control device of the tenth aspect, the motor is controlled so that the first response speed in the second control state is higher than the first response speed in the first control state.

In accordance with an eleventh aspect of the present disclosure, the human-powered vehicle control device according to the tenth aspect is configured so that the first response speed is increased as the steps of the first ratio changed during the predetermined period increase in number or as the steps of the first ratio changed by the signal received during the predetermined period increase in number.

In accordance with the human-powered vehicle control device of the eleventh aspect, the first response speed in the second control state is increased as the number of steps of the changed first ratio increases.

In accordance with a twelfth aspect of the present disclosure, the human-powered vehicle control device according to any one of the first to eleventh aspects is configured so that the electronic controller is configured to control the motor in accordance with the human drive force input to the human-powered vehicle. The electronic controller is configured to control the motor so that a second response speed of an output of the motor in a case in which the human drive force is decreased in the second control state is higher than the second response speed in the first control state.

In accordance with the human-powered vehicle control device of the twelfth aspect, the motor is controlled so that the second response speed in the second control state is higher than the second response speed in the first control state.

In accordance with a thirteenth aspect of the present disclosure, the human-powered vehicle control device according to the twelfth aspect is configured so that the second response speed is increased as the steps of the first ratio changed during the predetermined period increase in number or as the steps of the first ratio changed by the signal received during the predetermined period increase in number.

In accordance with the human-powered vehicle control device of the thirteenth aspect, the first response speed in the second control state is increased as the number of steps of the changed first ratio increases.

In accordance with a fourteenth aspect of the present disclosure, the human-powered vehicle control device according to any one of the first to thirteenth aspects is configured so that the electronic controller is configured to control the motor in the first control state in at least one of a case in which the first ratio is decreased and changed by only one step during the predetermined period and a case in which a signal is received for decreasing and changing the first ratio by one step during the predetermined period. The electronic controller is configured to control the motor in the second control state in at least one of a case in which the first ratio is decreased and changed by at least two steps during the predetermined period and a case in which a signal is received for decreasing and changing the first ratio by at least two steps during the predetermined period.

In accordance with the human-powered vehicle control device of the fourteenth aspect, the motor is controlled in a suitable manner for a case in which the first ratio is decreased and changed by one step and a case in which the first ratio is continuously decreased and changed by at least two steps.

In accordance with a fifteenth aspect of the present disclosure, the human-powered vehicle control device according to any one of the first to fourth aspects is configured so that the electronic controller is configured to control the motor in the first control state in at least one of a case in which the first ratio is increased and changed by only one step during the predetermined period and a case in which a signal is received for increasing and changing the first ratio by one step during the predetermined period. The electronic controller is configured to control the motor in the second control state in at least one of a case in which the first ratio is increased and changed by at least two steps during the predetermined period and a case in which a signal is received for increasing and changing the first ratio by at least two steps during the predetermined period.

In accordance with the human-powered vehicle control device of the fifteenth aspect, the motor is controlled in a suitable manner for a case in which the first ratio is changed by one step and a case in which the first ratio is continuously increased and changed by at least two steps.

A human-powered vehicle control device in accordance with a sixteenth aspect of the present disclosure comprises an electronic controller that controls a motor. In the human-powered vehicle control device, the motor assists in propulsion of a human-powered vehicle including a transmission configured to change, in steps, a first ratio of a rotational speed of a drive wheel to a rotational speed of a rotary body to which human drive force is input. The electronic controller is configured to change a control state of the motor from a third control state to a fourth control state that differs from the third control state in at least one of a case in which the first ratio is changed by the transmission and a case in which a signal is received for changing the first ratio. The electronic controller is configured to change the control state of the motor from the fourth control state to a fifth control state that differs from the fourth control state in accordance with a value related to at least one of a speed of the human-powered vehicle, the human drive force, an inclination angle of the human-powered vehicle, and a state of a rider of the human-powered vehicle.

In accordance with the human-powered vehicle control device of the sixteenth aspect, after the control state of the motor is changed from the third control state to the fourth control state, the control state is changed from the fourth control state to the fifth control state in accordance with the value related to at least one of the speed of the human-powered vehicle, the human drive force, the inclination angle of the human-powered vehicle, and the state of the rider of the human-powered vehicle. Therefore, after the control state of the motor is changed from the third control state to the fourth control state, the control state of the motor is automatically changed in accordance with the state of the human-powered vehicle.

In accordance with a seventeenth aspect of the present disclosure, the human-powered vehicle control device according to the sixteenth aspect is configured so that the electronic controller is configured to control the motor in accordance with the human drive force input to the human-powered vehicle. The electronic controller is configured to control the motor so that a second ratio of an assist force produced by the motor to the human drive force in the fourth control state is larger than the second ratio in the third control state.

In accordance with the human-powered vehicle control device of the seventeenth aspect, the motor is controlled so that the second ratio in the fourth control state is larger than the second ratio in the third control state.

In accordance with an eighteenth aspect of the present disclosure, in the human-powered vehicle control device according to the seventeenth aspect, the transmission is configured to change the first ratio in steps, and the second ratio is increased as the steps of the first ratio changed during the predetermined period increase in number or as the steps of the first ratio changed by the signal received during the predetermined period increase in number.

In accordance with the human-powered vehicle control device of the eighteenth aspect, the second ratio in the fourth control state is increased as the number of steps of the changed first ratio increases.

In accordance with a nineteenth aspect of the present disclosure, the human-powered vehicle control device according to the seventeenth aspect is configured so that the second ratio is increased as a change amount of the first ratio changed during the predetermined period increases or as a change amount of the first ratio changed by the signal received during the predetermined period increases.

In accordance with the human-powered vehicle control device of the nineteenth aspect, the second ratio in the fourth control state is increased as the change amount of the changed first ratio increases.

In accordance with a twentieth aspect of the present disclosure, the human-powered vehicle control device according to the sixteenth aspect is configured so that the electronic controller is configured to control the motor in accordance with the human drive force input to the human-powered vehicle. The electronic controller is configured to control the motor so that a second ratio of an assist force produced by the motor to the human drive force in the fourth control state is smaller than the second ratio in the third control state.

In accordance with the human-powered vehicle control device of the twentieth aspect, the motor is controlled so that the second ratio in the fourth control state is smaller than the second ratio in the third control state.

In accordance with a twenty-first aspect of the present disclosure, in the human-powered vehicle control device according to the twentieth aspect, the transmission is configured to change the first ratio in steps, and the second ratio is decreased as the steps of the first ratio changed during the predetermined period increase in number or as the steps of the first ratio changed by the signal received during the predetermined period increase in number.

In accordance with the human-powered vehicle control device of the twenty-first aspect, the second ratio in the fourth control state is decreased as the number of steps of the changed first ratio increases.

In accordance with a twenty-second aspect of the present disclosure, the human-powered vehicle control device according to the twentieth aspect is configured so that the second ratio is decreased as a change amount of the first ratio changed during the predetermined period increases or as a change amount of the first ratio changed by the signal received during the predetermined period increases.

In accordance with the human-powered vehicle control device of the twenty-second aspect, the second ratio in the fourth control state is decreased as the change amount of the changed first ratio increases.

In accordance with a twenty-third aspect of the present disclosure, the human-powered vehicle control device according to any one of the sixteenth to nineteenth aspects is configured so that the electronic controller is configured to control the motor in accordance with the human drive force input to the human-powered vehicle. The electronic controller is configured to control the motor so that a maximum value of an output of the motor is larger in the fourth control state than in the third control state.

In accordance with the human-powered vehicle control device of the twenty-third aspect, the motor is controlled so that the maximum value of the output of the motor in the fourth control state is larger than the maximum value of the output of the motor in the third control state.

In accordance with a twenty-fourth aspect of the present disclosure, in the human-powered vehicle control device according to the twenty-third aspect, the transmission is configured to change the first ratio in steps, and the maximum value is increased as the steps of the first ratio changed during the predetermined period increase in number or as the steps of the first ratio changed by the signal received during the predetermined period increase in number.

In accordance with the human-powered vehicle control device of the twenty-fourth aspect, the maximum value of the output of the motor in the fourth control state is increased as the number of steps of the changed first ratio increases.

In accordance with a twenty-fifth aspect of the present disclosure, the human-powered vehicle control device according to the twenty-third aspect is configured so that the maximum value is increased as a change amount of the first ratio changed during the predetermined period increases or as a change amount of the first ratio changed by the signal received during the predetermined period increases.

In accordance with the human-powered vehicle control device of the twenty-fifth aspect, the maximum value of the output of the motor in the fourth control state is increased as the change amount of the changed first ratio increases.

In accordance with a twenty-sixth aspect of the present disclosure, the human-powered vehicle control device according to any one of the sixteenth and twentieth to twenty-second aspects is configured so that the electronic controller is configured to control the motor in accordance with the human drive force input to the human-powered vehicle. The electronic controller is configured to control the motor so that a maximum value of an output of the motor is smaller in the fourth control state than in the third control state.

In accordance with the human-powered vehicle control device of the twenty-sixth aspect, the motor is controlled so that the maximum value of the output of the motor in the fourth control state is smaller than the maximum value of the output of the motor in the third control state.

In accordance with a twenty-seventh aspect of the present disclosure, in the human-powered vehicle control device according to the twenty-sixth aspect, the transmission is configured to change the first ratio in steps, and the maximum value is decreased as the steps of the first ratio changed during the predetermined period increase in number or as the steps of the first ratio changed by the signal received during the predetermined period increase in number.

In accordance with the human-powered vehicle control device of the twenty-seventh aspect, the maximum value of the output of the motor in the fourth control state is decreased as the number of steps of the changed first ratio increases.

In accordance with a twenty-eighth aspect of the present disclosure, the human-powered vehicle control device according to the twenty-sixth aspect is configured so that the maximum value is decreased as a change amount of the first ratio changed during the predetermined period increases or as a change amount of the first ratio changed by the signal received during the predetermined period increases.

In accordance with the human-powered vehicle control device of the twenty-eighth aspect, the maximum value of the output of the motor in the fourth control state is decreased as the change amount of the changed first ratio increases.

In accordance with a twenty-ninth aspect of the present disclosure, the human-powered vehicle control device according to any one of the sixteenth to twenty-eighth aspects is configured so that the electronic controller is configured to control the motor in accordance with the human drive force input to the human-powered vehicle. The electronic controller is configured to control the motor so that a first response speed of an output of the motor in a case in which the human drive force increases in the fourth control state is higher than the first response speed in the third control state.

In accordance with the human-powered vehicle control device of the twenty-ninth aspect, the motor is controlled so that the first response speed in the fourth control state is higher than the first response speed in the first control state.

In accordance with a thirtieth aspect of the present disclosure, in the human-powered vehicle control device according to the twenty-ninth aspect, the transmission is configured to change the first ratio in steps, and the first response speed is increased as the steps of the first ratio changed during the predetermined period increase in number or as the steps of the first ratio changed by the signal received during the predetermined period increase in number.

In accordance with the human-powered vehicle control device of the thirtieth aspect, the first response speed in the fourth control state increases as the number of steps of the changed first ratio increases.

In accordance with a thirty-first aspect of the present disclosure, the human-powered vehicle control device according to the twenty-ninth aspect is configured so that the first response speed is increased as a change amount of the first ratio changed during the predetermined period increases or as a change amount of the first ratio changed by the signal received during the predetermined period increases.

In accordance with the human-powered vehicle control device of the thirty-first aspect, the first response speed in the fourth control state is increased as the change amount of the changed first ratio increases.

In accordance with a thirty-second aspect of the present disclosure, the human-powered vehicle control device according to any one of the sixteenth to thirty-first aspects is configured so that the electronic controller is configured to control the motor in accordance with the human drive force input to the human-powered vehicle. The electronic controller is configured to control the motor so that a second response speed of an output of the motor in a case in which the human drive force decreases in the fourth control state is higher than the second response speed in the third control state.

In accordance with the human-powered vehicle control device of the thirty-second aspect, the motor is controlled so that the second response speed in the fourth control state is higher than the first response speed in the second control state.

In accordance with a thirty-third aspect of the present disclosure, in the human-powered vehicle control device according to the thirty-second aspect, the transmission is configured to change the first ratio in steps, and the second response speed is increased as the steps of the first ratio changed during the predetermined period increase in number or as the steps of the first ratio changed by the signal received during the predetermined period increase in number.

In accordance with the human-powered vehicle control device of the thirty-third aspect, the second response speed in the fourth control state is increased as the number of steps of the changed first ratio increases.

In accordance with a thirty-fourth aspect of the present disclosure, the human-powered vehicle control device according to the thirty-second aspect is configured so that the second response speed is increased as a change amount of the first ratio changed during the predetermined period increases or as a change amount of the first ratio changed by the signal received during the predetermined period increases.

In accordance with the human-powered vehicle control device of the thirty-fourth aspect, the second response speed in the fourth control state is increased as the change amount of the changed first ratio increases.

In accordance with a thirty-fifth aspect of the present disclosure, the human-powered vehicle control device according to any one of the sixteenth to thirty-fourth aspects is configured so that the fourth control state includes a first control state and a second control state that differs from the first control state, the electronic controller is configured to control the motor in the first control state in at least one of a case in which the first ratio is decreased and changed by only one step during the predetermined period and a case in which a signal is received for decreasing and changing the first ratio by one step during the predetermined period. The electronic controller is configured to control the motor in the second control state in at least one of a case in which the first ratio is decreased and changed by at least two steps during the predetermined period and a case in which a signal is received for decreasing and changing the first ratio by at least two steps during the predetermined period.

In accordance with the human-powered vehicle control device of the thirty-fifth aspect, the motor is controlled in a suitable manner for a case in which the first ratio is changed by one step and a case in which the first ratio is continuously changed by at least two steps.

In accordance with a thirty-sixth aspect of the present disclosure, the human-powered vehicle control device according to any one of the sixteenth to thirty-fourth aspects is configured so that the fourth control state includes a first control state and a second control state that differs from the first control state, the electronic controller is configured to control the motor in the first control state in at least one of a case in which the first ratio is increased and changed by only one step during the predetermined period and a case in which a signal is received for increasing and changing the first ratio by one step during the predetermined period. The electronic controller is configured to control the motor in the second control state in at least one of a case in which the first ratio is increased and changed by at least two steps during the predetermined period and a case in which a signal is received for increasing and changing the first ratio by at least two steps during the predetermined period.

In accordance with the human-powered vehicle control device of the thirty-sixth aspect, the motor is controlled in a suitable manner for a case in which the first ratio is changed by one step and a case in which the first ratio is continuously increased and changed by at least two steps.

In accordance with a thirty-seventh aspect of the present disclosure, the human-powered vehicle control device according to any one of the sixteenth to thirty-fifth aspects is configured so that the electronic controller is configured to change the control state of the motor from the fourth control state to the fifth control state in a case in which an increased amount of a value related to a vehicle speed becomes greater than or equal to a predetermined first value in the fourth control state or in a case in which a value related to the vehicle speed becomes greater than or equal to a predetermined second value in the fourth control state.

In accordance with the human-powered vehicle control device of the thirty-seventh aspect, the control state of the motor is changed from the fourth control state to the fifth control state in a case in which the increased amount of the value related to the vehicle speed is greater than or equal to the predetermined first value or in accordance with an increase in vehicle speed.

In accordance with a thirty-eighth aspect of the present disclosure, the human-powered vehicle control device according to any one of the sixteenth to thirty-seventh aspects is configured so that the electronic controller is configured to change the control state of the motor from the fourth control state to the fifth control state in a case in which a decreased amount of a value related to the human drive force becomes greater than or equal to a predetermined third value in the fourth control state or in a case in which a value related to the human drive force becomes less than or equal to a predetermined fourth value in the fourth control state.

In accordance with the human-powered vehicle control device of the thirty-eighth aspect, the control state of the motor is changed from the fourth control state to the fifth control state in accordance with a decrease in the human drive force.

In accordance with a thirty-ninth aspect of the present disclosure, the human-powered vehicle control device according to any one of the sixteenth to thirty-eighth aspects is configured so that the electronic controller is configured to change the control state of the motor from the fourth control state to the fifth control state in a case in which a decreased amount of a value related to an inclination angle of the human-powered vehicle becomes greater than or equal to a predetermined fifth value in the fourth control state or in a case in which a value related to an inclination angle of the human-powered vehicle becomes less than or equal to a predetermined sixth value in the fourth control state.

In accordance with the human-powered vehicle control device of the thirty-ninth aspect, the control state of the motor can be changed from the fourth control state to the fifth control state in accordance with a decrease in the inclination angle.

In accordance with a fortieth aspect of the present disclosure, the human-powered vehicle control device according to any one of the sixteenth to thirty-ninth aspects is configured so that a state of a rider of the human-powered vehicle includes a heart rate of the rider. The electronic controller is configured to change the control state of the motor from the fourth control state to the fifth control state in a case in which a decreased amount of a value related to the heart rate becomes greater than or equal to a predetermined seventh value in the fourth control state or in a case in which a value related to the heart rate of the rider becomes less than or equal to a predetermined eighth value in the fourth control state.

In accordance with the human-powered vehicle control device of the fortieth aspect, the control state of the motor is changed from the fourth control state to the fifth control state in accordance with a decrease in the heart rate.

In accordance with a forty-first aspect of the present disclosure, the human-powered vehicle control device according to any one of the sixteenth to fortieth aspects is configured so that the fifth control state includes the third control state.

In accordance with the human-powered vehicle control device of the forty-first aspect, after the control state of the motor is changed from the third control state to the fourth control state, the control state is changed from the fourth control state to the third control state in accordance with the value related to at least one of the speed of the human-powered vehicle, the human drive force, the inclination angle of the human-powered vehicle, and the state of the rider of the human-powered vehicle.

A human-powered vehicle control device in accordance with a forty-second aspect of the present disclosure comprises an electronic controller that is configured to control a motor. In the human-powered vehicle control device, the motor assists in propulsion of a human-powered vehicle including a transmission configured to change a first ratio of a rotational speed of a drive wheel to a rotational speed of a rotary body to which human drive force is input. The electronic controller is configured to control the motor in a first control state in at least one of a case in which the first ratio is changed so that a change amount of the first ratio in a predetermined period becomes less than or equal to a first change amount and a case in which a signal is received for changing the first ratio so that a change amount of the first ratio in the predetermined period becomes less than or equal to the first change amount. The electronic controller is configured to control the motor in a second control state that differs from the first control state in at least one of a case in which the first ratio is changed so that a change amount of the first ratio in the predetermined period exceeds the first change amount and a case in which a signal is received for changing the first ratio so that a change amount of the first ratio in the predetermined period exceeds the first change amount.

In accordance with the human-powered vehicle control device of the forty-second aspect, the motor is controlled in a suitable manner for a case in which the change amount of the first ratio in the predetermined period is less than or equal to the first change amount and a case in which the change amount of the first ratio in the predetermined period exceeds the first change amount.

In accordance with a forty-third of the present disclosure, the human-powered vehicle control device according to any one of the first to forty-second aspects further comprises a first detector that outputs a signal corresponding to an operation of an operation unit used to operate the transmission, and is configured so that the electronic controller is configured to change a control state of the motor in accordance with the output of the first detector.

In accordance with the human-powered vehicle control device of the forty-third aspect, the operation of the transmission is suitably detected by the first detector.

In accordance with a forty-fourth aspect of the present disclosure, the human-powered vehicle control device according to any one of the first to forty-third aspects further comprises a second detector that outputs a signal corresponding to a state of the transmission, and is configured so that the electronic controller is configured to change a control state of the motor in accordance with the output of the second detector.

In accordance with the human-powered vehicle control device of the forty-fourth aspect, the state of the transmission is suitably detected by the second detector.

In accordance with a forty-fifth aspect of the present disclosure, in the human-powered vehicle control device according to any one of the first to forty-fourth aspects, the transmission is configured to be driven by an electric actuator. The electronic controller is configured to control the electric actuator.

In accordance with the human-powered vehicle control device of the forty-fifth aspect, the transmission is operated by the electric actuator.

The human-powered vehicle control device in accordance with the present disclosure sets a suitable traveling state for a human-powered vehicle.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the human-powered vehicle field from this disclosure that the following descriptions of the embodiments are provided for illustration only and not for the purpose of limiting the invention as defined by the appended claims and their equivalents.

A human-powered vehicle control device 40 in accordance with one embodiment will now be described with reference to FIGS. 1 to 11. Hereinafter, the human-powered vehicle control device 40 will simply be referred to as the control device 40. The control device 40 is provided in the human-powered vehicle 10. The human-powered vehicle 10 is a vehicle that can be driven by at least human drive force. The human-powered vehicle 10 includes, for example, a bicycle. The human-powered vehicle 10 also includes, for example, a unicycle and a vehicle having three or more wheels, and the number of wheels is not limited. The human-powered vehicle 10 includes various types of bicycles such as a mountain bike, a road bike, a city bike, a cargo bike, a recumbent bike, and, and an electric assist bicycle (E-bike). The human-powered vehicle 10 described hereafter is a bicycle.

Figure 1:
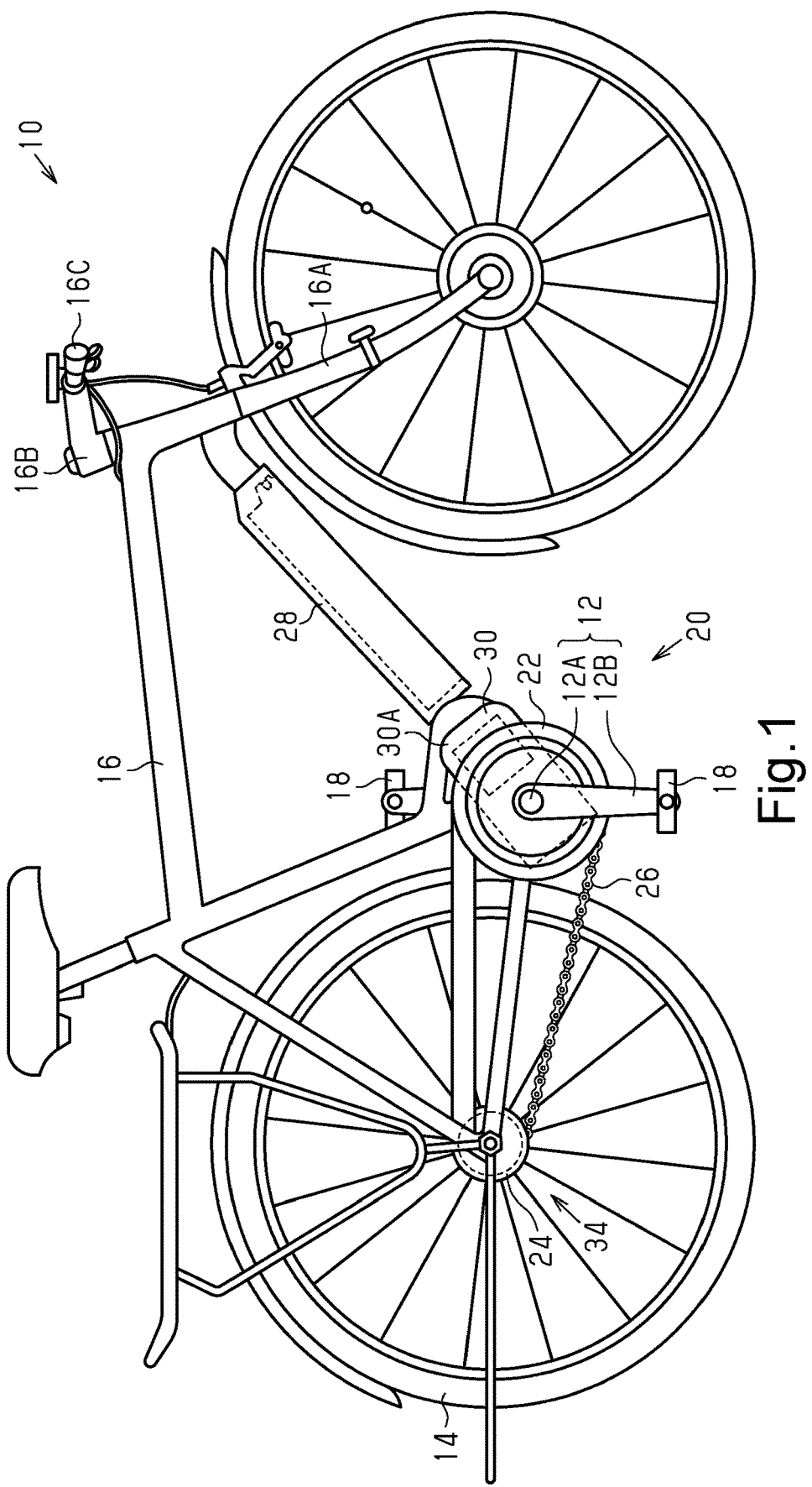
FIG. 1 is a side elevational view of a human-powered vehicle including a human-powered vehicle control device in accordance with one illustrated embodiment.
Figure 2:
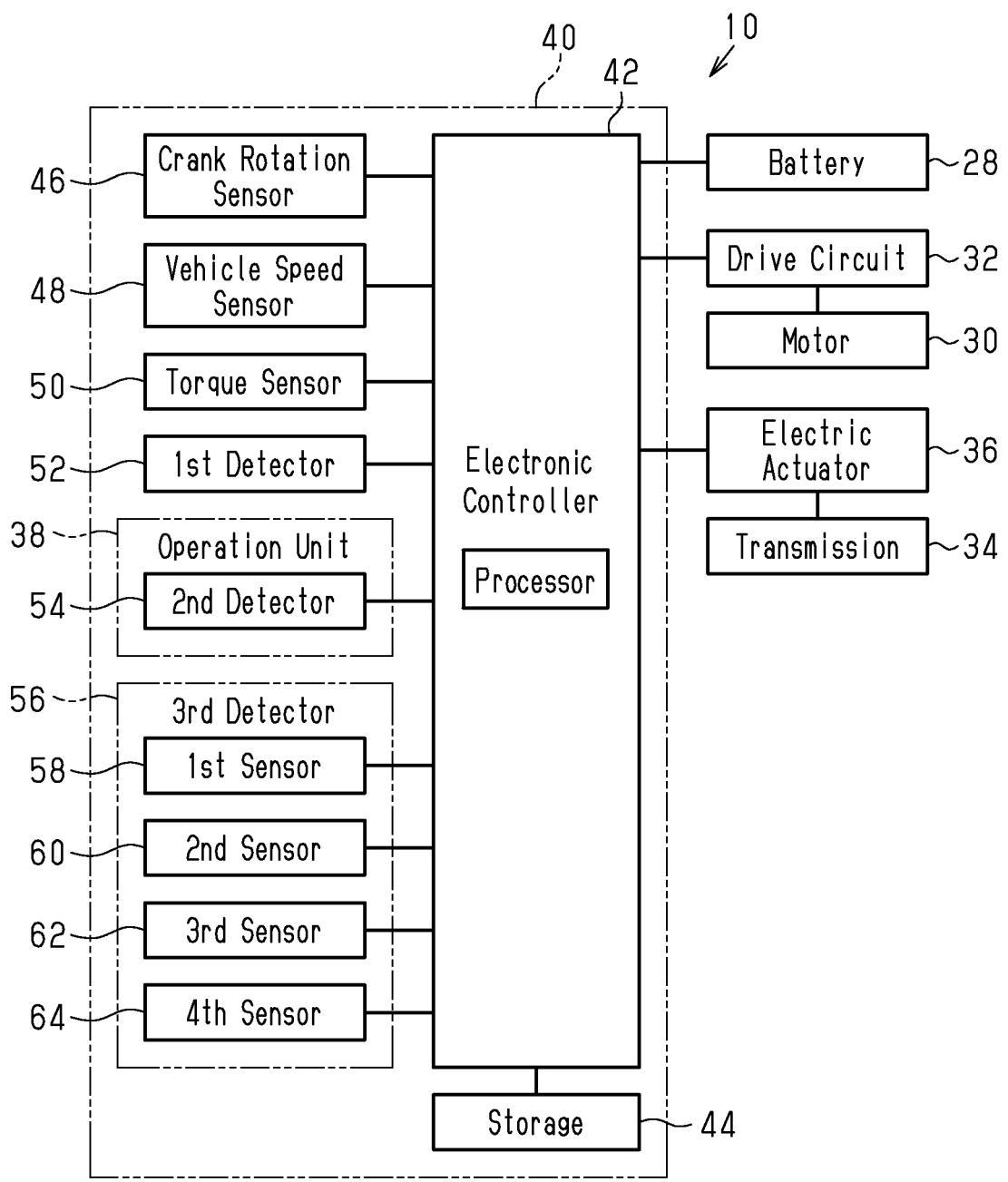
FIG. 2 is a block diagram showing an electrical configuration of the human-powered vehicle control device in accordance with the illustrated embodiment.

As shown in FIG. 1, the human-powered vehicle 10 includes a crank 12 and a drive wheel 14. The human-powered vehicle 10 further includes a frame 16. A human drive force H is input to the crank 12. The crank 12 includes a crankshaft 12A rotatable relative to the frame 16 and a crank arm 12B provided on each of the opposite axial ends of the crankshaft 12A. A pedal 18 is connected to each of the crank arms 12B. The drive wheel 14 is driven by the rotation of the crank 12. The drive wheel 14 is supported by the frame 16. The crank 12 and the drive wheel 14 are connected by a drive mechanism 20. The drive mechanism 20 includes a first rotary body 22 coupled to the crankshaft 12A. The crankshaft 12A and the first rotary body 22 can be coupled by a first one-way clutch. The first one-way clutch is configured to rotate the first rotary body 22 forward in a case in which the crank 12 rotates forward and not rotate the first rotary body 22 backward in a case in which the crank 12 rotates backward. The first rotary body 22 includes a sprocket, a pulley, or a bevel gear. The drive mechanism 20 further includes a second rotary body 24 and a linking member 26. The linking member 26 transmits the rotational force of the first rotary body 22 to the second rotary body 24. The linking member 26 includes, for example, a chain, a belt, or a shaft.

The second rotary body 24 is connected to the drive wheel 14. The second rotary body 24 includes a sprocket, a pulley, or a bevel gear. A second one-way clutch is preferably provided between the second rotary body 24 and the drive wheel 14. The second one-way clutch is configured to rotate the drive wheel 14 forward in a case in which the second rotary body 24 rotates forward and not rotate the drive wheel 14 backward in a case in which the second rotary body 24 rotates backward.

The human-powered vehicle 10 includes a front wheel and a rear wheel. The front wheel is attached to the frame 16 by a front fork 16A. A handlebar 16C is connected to the front fork 16A by a stem 16B. In the following embodiment, the rear wheel will be referred to as the drive wheel 14. However, the front wheel can be the drive wheel 14.

The human-powered vehicle 10 further includes a battery 28. The battery 28 includes one or more battery cells. The battery cell includes a rechargeable battery. The battery 28 is provided on the human-powered vehicle 10 and supplies power to other electric components such as a motor 30 and the control device 40, which are electrically connected to the battery 28 by wires. The battery 28 is connected to an electronic controller 42 of the control device 40. Hereinafter, the electronic controller 42 will simply be referred to as the controller 42. The battery 28 communicates with the controller 42 through wired or wireless connection. The battery 28 is configured to communicate with the controller 42 though, for example, power line communication (PLC). The battery 28 can be attached to the outside of the frame 16 or at least partially accommodated in the frame 16.

The human-powered vehicle 10 further includes a motor 30 and a drive circuit 32 for the motor 30. The motor 30 and the drive circuit 32 are preferably provided in the same housing 30A. The drive circuit 32 controls power supplied from the battery 28 to the motor 30. The drive circuit 32 is connected to the controller 42 to communicate with the controller 42 through wired or wireless connection. The drive circuit 32 is configured to communicate with the controller 42, for example, through serial communication. The drive circuit 32 drives the motor 30 in accordance with a control signal from the controller 42. The motor 30 is a propulsion assist motor that assists in propulsion of the human-powered vehicle 10. The motor 30 includes an electric motor. The motor 30 is provided in a power transmission path of the human drive force H extending from the pedals 18 to the rear wheel or provided to transmit rotation to the front wheel. The motor 30 is provided on the frame 16, the rear wheel, or the front wheel of the human-powered vehicle 10. In one example, the motor 30 is coupled to a power transmission path extending from the crankshaft 12A to the first rotary body 22. A one-way clutch is preferably provided on the power transmission path between the motor 30 and the crankshaft 12A so that the motor 30 does is not rotated by the rotational force of the crank 12 in a case in which the crankshaft 12A is rotated in the direction in which the human-powered vehicle 10 moves forward. The housing 30A on which the motor 30 and the drive circuit 32 are provided can be provided with components other than the motor 30 and the drive circuit 32, for example, a reduction gear that reduces the speed of the rotation of the motor 30 and outputs the rotation.

The human-powered vehicle 10 includes a transmission 34. In the present embodiment, the transmission 34 is configured to change, in steps, a first ratio R of a rotational speed of the drive wheel 14 to a rotational speed of a rotary body to which human drive force H is input. The rotary body to which the human drive force H is input includes the crank 12. The transmission 34 is configured to be driven by an electric actuator 36. The controller 42 controls the electric actuator 36. The transmission 34, together with the electric actuator 36 forms a transmission device. The electric actuator 36 includes an electric motor. The transmission 34 is used to change the first ratio R of the rotational speed of the drive wheel 14 to the rotational speed N of the crank 12. In the present embodiment, the transmission 34 is configured to change the first ratio R in steps. The electric actuator 36 causes the transmission 34 to perform a shift operation. The transmission 34 is controlled by the controller 42. The electric actuator 36 is connected to the controller 42 to communicate with the controller 42 through wired or wireless connection. The electric actuator 36 is configured to communicate with the controller 42, for example, by power line communication (PLC). The electric actuator 36 shifts the transmission ratio with the transmission 34 in accordance with a control signal from the controller 42. The transmission 34 includes at least one of an internal transmission device and an external transmission device (derailleur).

The control device 40 includes the controller 42. The terms "controller" and "electronic controller" as used herein refer to hardware that executes a software program and does not include a human. The controller 42 includes at least one processor that performs a predetermined control program. The processor is, for example, a central processing unit (CPU) or a micro-processing unit (MPU). The controller 42 can include one or more microcomputers with one or more processors. The controller 42 can include a plurality of processors located at separate positions. The control device 40 further includes a storage (memory device) 44. The storage 44 stores various control programs and information used for various control processes. The storage 44 includes any computer storage device or any non-transitory computer-readable medium with the sole exception of a transitory, propagating signal. For example, the storage 44 includes a nonvolatile memory and a volatile memory. The controller 42 and the storage 44 are, for example, provided on the housing 30A on which the motor 30 is provided.

The control device 40 further includes a crank rotation sensor 46, a vehicle speed sensor 48, and a torque sensor 50.

The crank rotation sensor 46 is used to detect the rotational speed N of the crank 12 of the human-powered vehicle 10. The crank rotation sensor 46 is attached to, for example, the frame 16 of the human-powered vehicle 10 or the housing 30A on which the motor 30 is provided. The crank rotation sensor 46 includes a magnetic sensor that outputs a signal corresponding to the intensity of a magnetic field. An annular magnet, of which the magnetic field intensity changes in the circumferential direction, is provided on the crankshaft 12A or the power transmission path between the crankshaft 12A and the first rotary body 22. The crank rotation sensor 46 can be any sensor that can produce a signal that is indicative of the rotational speed N of the crank 12. The crank rotation sensor 46 is connected to the controller 42 to communicate with the controller 42 through wired or wireless connection. The crank rotation sensor 46 outputs a signal corresponding to the rotational speed N of the crank 12 to the controller 42. The crank rotation sensor 46 can be provided on a member that rotates integrally with the crankshaft 12A in the power transmission path of the human drive force H from the crankshaft 12A to the first rotary body 22. For example, the crank rotation sensor 46 can be provided on the first rotary body 22 in a case in which the first one-way clutch is not provided between the crankshaft 12A and the first rotary body 22. The crank rotation sensor 46 can be used to detect a vehicle speed V of the human-powered vehicle 10. In this case, the controller 42 calculates the rotational speed of the drive wheel 14 in accordance with the rotational speed N of the crank 12 detected by the crank rotation sensor 46 and the first ratio R to obtain the vehicle speed V of the human-powered vehicle 10. Information related to the first ratio R is stored in advance in the storage 44.

In a case in which the transmission 34 for changing the first ratio R is provided on the human-powered vehicle 10, the controller 42 can calculate the first ratio R in accordance with the vehicle speed V of the human-powered vehicle 10 and the rotational speed N of the crank 12. In this case, information related to the circumferential length of the drive wheel 14, the diameter of the drive wheel 14, or the radius of the drive wheel 14 is stored in advance in the storage 44. In a case in which the rotational speed of the drive wheel 14 is detected by the crank rotation sensor 46 and the human-powered vehicle 10 includes the transmission 34, the crank rotation sensor 46 preferably includes a shift sensor for detecting the first ratio R. The shift sensor detects the current shift stage of the transmission 34. The relationship between the shift stage and the first ratio R is stored in advance in the storage 44. The controller 42 thus obtains the current first ratio R from the detection result of the shift sensor. The controller 42 can calculate the rotational speed N of the crank 12 by dividing the rotational speed of the drive wheel 14 by the first ratio R. In this case, the vehicle speed sensor 48 can be used as the crank rotation sensor 46.

The vehicle speed sensor 48 is used to detect the rotational speed of the wheel. The vehicle speed sensor 48 is electrically connected to the controller 42 in a wired or wireless manner. The vehicle speed sensor 48 is connected to the controller 42 to communicate with the controller 42 through wired or wireless connection. The vehicle speed sensor 48 outputs a signal corresponding to the rotational speed of the wheel to the controller 42. The vehicle speed sensor 48 can be any sensor that can produce a signal that is indicative of the rotational speed of the wheel. The controller 42 calculates the vehicle speed V of the human-powered vehicle 10 based on the rotational speed of the wheel. The controller 42 stops the motor 30 in a case in which the vehicle speed V becomes higher than or equal to a predetermined value. The predetermined value is, for example, 25 kilometers per hour or 45 kilometers per hour. The vehicle speed sensor preferably includes a magnetic reed forming a reed switch or a Hall element. The vehicle speed sensor can be mounted on a chain stay of the frame 16 to detect a magnet attached to the rear wheel or can be provided on the front fork 16A to detect a magnet attached to the front wheel. Thus, in the case of a reed switch or a Hall element, the vehicle speed sensor 48 indirectly detects the rotational speed of the wheel by detecting a magnet attached to the wheel. Alternatively, the vehicle speed sensor 48 can directly detect the rotational speed of the wheel by using a speedometer gear assembly that is directly rotated by the wheel. In another example, the vehicle speed sensor 48 includes a GPS receiver. The controller 42 can detect the vehicle speed V of the human-powered vehicle 10 in accordance with the GPS information acquired by the GPS receiver, map information recorded in advance in the storage 44, and the time. The controller 42 preferably includes a time measuring circuit for measuring time.

The torque sensor 50 is used to detect torque TH of the human drive force H. The torque sensor 50 is provided, for example, on the housing on which the motor 30 is provided. The torque sensor 50 detects the torque TH of the human drive force H input to the crank 12. For example, in a case in which the first one-way clutch is provided in the power transmission path, the torque sensor 50 is provided at the upstream side of the first one-way clutch. The torque sensor 50 includes a strain sensor, a magnetostrictive sensor, or the like. The strain sensor includes a strain gauge. In a case in which the torque sensor 50 includes a strain sensor, the strain sensor is preferably provided on an outer circumferential portion of the rotary body included in the power transmission path. The torque sensor 50 can be any sensor that can produce a signal that is indicative of the human drive force H inputted to the crank 12. The torque sensor 50 can include a wireless or wired communicator. The communicator of the torque sensor 50 is configured to communicate with the controller 42.

Preferably, the control device 40 further includes a first detector 52 that outputs a signal corresponding to the operation of an operation unit 38, which is configured to operate the transmission 34. The term "detector" as used herein refers to a hardware device or instrument designed to detect the presence of a particular object or substance and to emit a signal in response. The term "detector" as used herein do not include a human. The controller 42 changes the control state of the motor 30 in accordance with the output of the first detector 52. The operation unit 38 is operated to change the operational state of the transmission 34. The operation unit 38 is connected to the controller 42 to communicate with the controller 42 through wired or wireless connection. The operation unit 38 is configured to communicate with the controller 42 though, for example, power line communication (PLC). The operation unit 38 includes, for example, an operation member, the first detector 52 that detects the movement of the operation member, and an electric circuit that communicates with the controller 42 in accordance with an output signal of the first detector 52. In a case in which the operation member is operated by a user, the first detector 52 transmits the output signal to the controller 42. The operation member and the first detector 52 that detects movement of the operation member can be configured by a push switch, a lever type switch, or a touch panel. The operation unit 38 is provided, for example, on the handlebar 16C.

Preferably, the control device 40 further includes a second detector 54 that outputs a signal corresponding to the state of the transmission 34. The controller 42 changes the control state of the motor 30 in accordance with the output of the second detector 54. The second detector 54 detects the current shift stage of the transmission 34. The relationship between the shift stage and the first ratio R is stored in advance in the storage 44. Thus, the controller 42 can obtain the current first ratio R from the detection result of the second detector 54. In a case in which the crank rotation sensor 46 includes a shift sensor, the second detector 54 is configured in the same manner as the shift sensor of the crank rotation sensor 46. The shift sensor of the crank rotation sensor 46 can be used as the second detector 54. However, the second detector 54 can be separate from the shift sensor of the crank rotation sensor 46.

Preferably, the control device 40 further includes a third detector 56 that detects a value related to at least one of the vehicle speed V of the human-powered vehicle 10, the human drive force H, the inclination angle G of the human-powered vehicle, and the state of the rider of the human-powered vehicle 10. The controller 42 changes the control state of the motor 30 in accordance with the output of the third detector 56.

The third detector 56 includes at least one of a first sensor 58, a second sensor 60, a third sensor 62, and a fourth sensor 64.

The first sensor 58 is used to detect the vehicle speed V of the human-powered vehicle 10. The first sensor 58 is configured in the same manner as the vehicle speed sensor 48. The vehicle speed sensor 48 can be used as the first sensor 58, but the first sensor 58 can be configured separately from the vehicle speed sensor 48.

The second sensor 60 is used to detect the human drive force H. The human drive force H detected by the second sensor 60 includes the torque TH or the power WH of the human drive force H. In a case in which the torque TH of the human drive force H is detected using the second sensor 60, the second sensor 60 is configured in the same manner as the torque sensor 50. The torque sensor 50 can be used as the second sensor 60. However, the second sensor 60 can be separate from the torque sensor 50. In a case in which the power WH of the human drive force H is detected using the second sensor 60, the second sensor 60 is configured in the same manner as the torque sensor 50 and the crank rotation sensor 46. The torque sensor 50 and the crank rotation sensor 46 can be used as the second sensor 60. However, the second sensor 60 can be separate from the torque sensor 50 and the crank rotation sensor 46.

The third sensor 62 is used to detect the tilt of the human-powered vehicle 10. An inclination angle G of the road surface on which the human-powered vehicle 10 travels can be detected by the third sensor 62. The inclination angle G of the road surface on which the human-powered vehicle 10 travels can be detected by the inclination angle in the traveling direction of the human-powered vehicle 10. The inclination angle G of the road surface on which the human-powered vehicle 10 travels corresponds to the inclination angle of the human-powered vehicle 10. In one example, the third sensor 62 includes an inclination sensor. An example of an inclination sensor is a gyro sensor or an acceleration sensor. In another example, the third sensor 62 includes a global positioning system (GPS) receiver. The third sensor 62 can be any sensor or device that can produce a signal that is indicative of the inclination angle G of the road surface on which the human-powered vehicle 10 travels. The controller 42 can calculate the inclination angle G of the road surface on which the human-powered vehicle 10 travels from the GPS information obtained by the GPS receiver and the road surface gradient included in the map information, which is recorded in advance in the storage 44.

The fourth sensor 64 is used to detect the state of the rider of the human-powered vehicle 10. The fourth sensor 64 includes, for example, a heart rate sensor. The heart rate sensor detects the heart rate of the rider. The heart rate sensor is configured to be attachable to, for example, the body of the rider. The fourth sensor 64 can be any sensor or device that can produce a signal that is indicative of the heart rate of the rider. The heart rate sensor can include a wireless or wired communicator. The communicator of the fourth sensor 64 is configured to communicate with the controller 42. The communicator of the fourth sensor 64 can be configured to communicate with, for example, a cycle computer, and the information detected by the fourth sensor 64 can be transmitted from the cycle computer to the controller 42.

For example, the controller 42 controls the motor 30 so that the assist force produced by the motor 30 to the human drive force H becomes equal to a predetermined ratio. For example, the controller 42 can control the motor 30 so that the power WM (watt) of the motor 30 to the power WH (watt) of the human drive force H becomes equal to a predetermined ratio. The controller 42 controls the motor 30 in a plurality of control modes having different second ratios A of the output of the motor 30 to the human drive force H. A ratio AW of the power WM of the output of the motor 30 to the power WH of the human drive force H of the human-powered vehicle 10 can be referred to as the second ratio A. The power WH of the human drive force H is calculated by multiplying the human drive force H and the rotational speed N of the crank 12. The controller 42 can control the motor 30 so that the output torque TM of the assist force produced by the motor 30 to the torque TH of the human drive force H of the human-powered vehicle 10 becomes equal to a predetermined ratio. A torque ratio AT of the output torque TM of the motor 30 to the torque TH of the human drive force H of the human-powered vehicle 10 can be referred to as the second ratio A. In a case in which the output of the motor 30 is input to the power transmission path of the human drive force H via the reduction gear, the output of the reduction gear is referred to as the output of the motor 30. The controller 42 outputs a control command to the drive circuit 32 of the motor 30 in accordance with the power WH or the torque TH of the human drive force H. The control command includes, for example, a torque command value.

The controller 42 controls the motor 30 so that the output of the motor 30 becomes less than or equal to a predetermined value. The output of the motor 30 includes the output torque TM of the motor 30. The controller 42 can control the motor 30 so that the ratio AW becomes less than or equal to a predetermined value AW1. In one example, the predetermined value AW1 is 500 watts. In another example, the predetermined value AW1 is 300 watts. The controller 42 can control the motor 30 so that the torque ratio AT becomes less than or equal to the predetermined torque ratio AT1. In one example, the predetermined torque ratio AT1 is 300%.

The controller 42 controls the motor 30 that assists in the propulsion of the human-powered vehicle 10 including the transmission 34. The controller 42 controls the motor 30 in the first control state in at least one of a case in which the first ratio R is changed by only one step during a predetermined period and a case in which a signal is received for changing the first ratio R by one step during the predetermined period. The controller 42 controls the motor 30 in the second control state that differs from the first control state in at least one of a case in which the first ratio R is changed by two or more steps during the predetermined period and a case in which a signal is received for changing the first ratio R by two or more steps during the predetermined period.

Preferably, the controller 42 controls the motor 30 in the first control state in at least one of a case in which the first ratio R is decreased and changed by only one step during the predetermined period and a case in which a signal is received for decreasing and changing the first ratio R by one step during the predetermined period. The controller 42 controls the motor 30 in the second control state in at least one of a case in which the first ratio R is decreased and changed by two or more steps during the predetermined period and a case in which a signal is received for decreasing and changing the first ratio R by two or more steps during the predetermined period. Preferably, the controller 42 controls the motor 30 in the first control state in at least one of a case in which the first ratio R is increased and changed by only one step during the predetermined period and a case in which a signal is received for increasing and changing the first ratio R by one step during the predetermined period. The controller 42 controls the motor 30 in the second control state in at least one of a case in which the first ratio R is increased and changed by two or more steps during the predetermined period and a case in which a signal is received for increasing and changing the first ratio R by two or more steps during the predetermined period. The controller 42 can control the motor 30 in the first control state or the second control state in accordance with the step of the changed first ratio R if one of a case in which the first ratio R is decreased and changed and a case in which the first ratio R is increased and changed occurs. Further, the controller 42 can control the motor 30 in the same control state irrespective of the step of the changed first ratio R if the other one of a case in which the first ratio R is decreased and changed and a case in which the first ratio R is increased and changed occurs. The same control state includes, for example, the first control state.

Figure 3:
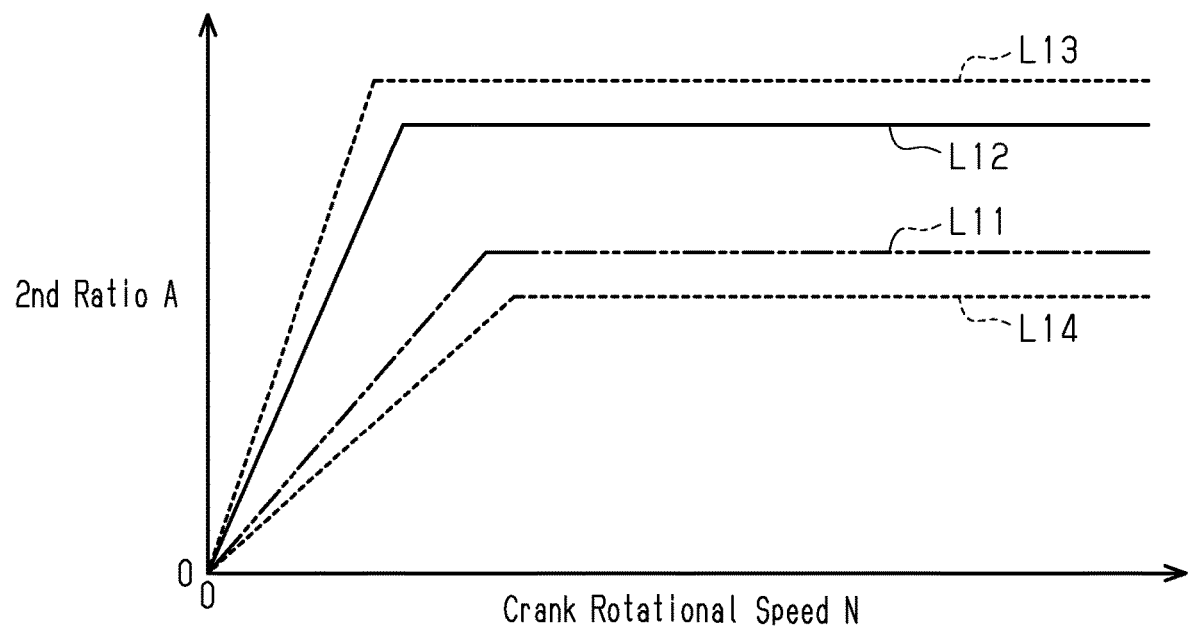
FIG. 3 is a map showing an example of the relationship between a rotational speed of a crank and a second ratio stored in a storage of FIG. 2.

In a first example, the controller 42 controls the motor 30 in accordance with the human drive force H input to the human-powered vehicle 10. The controller 42 controls the motor 30 so that the second ratio A of the assist force produced by the motor 30 to the human drive force H in the second control state is larger than the second ratio A in the first control state. For example, a double-dashed line L11 in FIG. 3 shows an example of the relationship between the rotational speed N of the crank 12 and the second ratio A1 in the first control state. A solid line L12 in FIG. 3 shows an example of the relationship between the rotational speed N of the crank 12 and the second ratio A2 in the second control state. The second ratio A2 is increased as the steps of the first ratio R changed during the predetermined period increase in number or as the steps of the first ratio R changed by the signal received during the predetermined period increase in number. In the example of FIG. 3, the controller 42 controls the motor 30 so that the second ratio A2 with respect to the rotational speed N of the crank 12 becomes the solid line L12 in a case in which the step of the first ratio R changed by the signal received during the predetermined period within the predetermined period is one step in the second control state. The controller 42 controls the motor 30 so that the second ratio A2 with respect to the rotational speed N of the crank 12 becomes a broken line L13 in a case in which the step of the first ratio R changed by the signal received during the predetermined period within the predetermined period is two steps in the second control state. The controller 42 can determine the second ratio A in accordance with the torque TH instead of the rotational speed N of the crank 12 in the first control state and the second control state. In this case, the relationship in which the rotational speed N of the crank 12 in FIG. 3 is replaced by the torque TH can be the relationship between the torque TH and the second ratio A in the first control state and the second control state.

In a second example, the controller 42 controls the motor 30 in accordance with the human drive force H input to the human-powered vehicle 10. The controller 42 controls the motor 30 so that the second ratio A of the assist force produced by the motor 30 to the human drive force H in the second control state is smaller than the second ratio A in the first control state. For example, the solid line L12 in FIG. 3 shows an example of the relationship between the rotational speed N of the crank 12 and the second ratio A1 in the first control state. The double-dashed line L11 in FIG. 3 shows an example of the relationship between the rotational speed N of the crank 12 and the second ratio A2 in the second control state. The second ratio A2 is decreased as the steps of the first ratio R changed during the predetermined period increase in number or as the steps of the first ratio R changed by the signal received during the predetermined period increase in number. In the example of FIG. 3, the controller 42 controls the motor 30 so that the second ratio A2 with respect to the rotational speed N of the crank 12 becomes the double-dashed line L11 in a case in which the step of the first ratio R changed by the signal received during the predetermined period within the predetermined period is one step in the second control state. The controller 42 controls the motor 30 so that the second ratio A2 with respect to the rotational speed N of the crank 12 becomes a broken line L14 in a case in which the step of the first ratio R changed by the signal received during the predetermined period within the predetermined period is two steps in the second control state.

Figure 4:
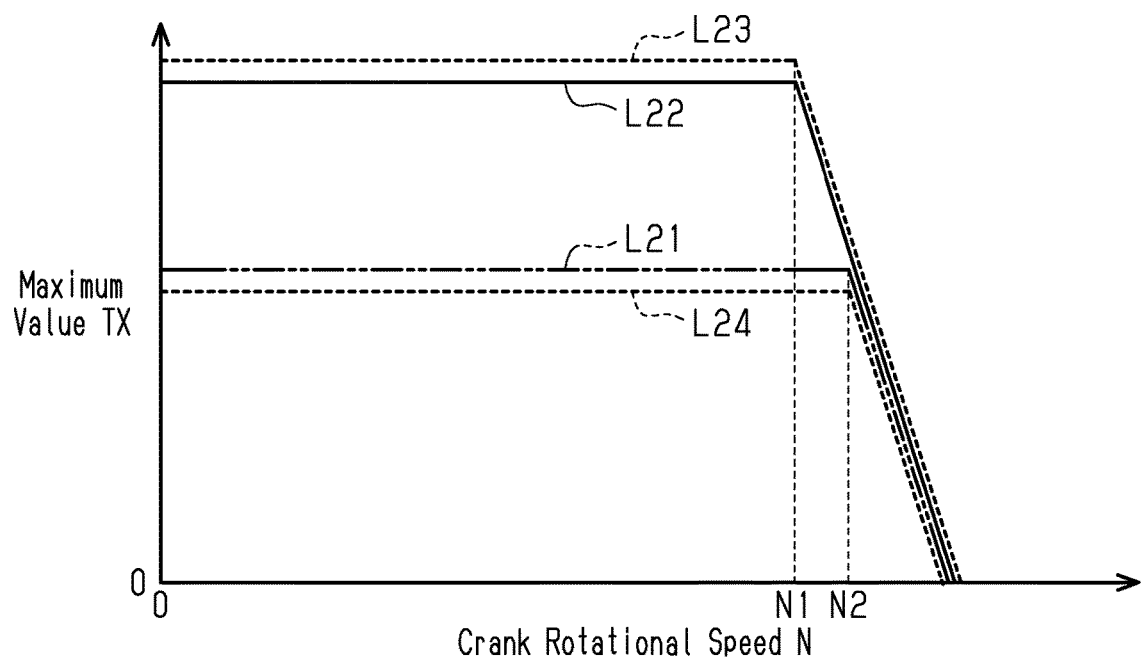
FIG. 4 is a map showing an example of the relationship between the rotational speed of the crank and a maximum value of an output of a motor stored in the storage of FIG. 2.

In a third example, the controller 42 controls the motor 30 in accordance with the human drive force H input to the human-powered vehicle 10. The controller 42 controls the motor 30 so that a maximum value TX of the output of the motor 30 is larger in the second control state than in a case of the first control state. For example, a double-dashed line L21 in FIG. 4 shows an example of the relationship between the rotational speed N of the crank 12 and the maximum value TX1 in the first control state. In the double-dashed line L21 in FIG. 4, the maximum value TX1 in the first control state is a constant value in the range where the rotational speed N of the crank 12 is less than the first speed N1. After reaching the first speed N1, the maximum value TX1 decreases as the rotational speed N of the crank 12 increases. A solid line L22 in FIG. 4 shows an example of the relationship between the rotational speed N of the crank 12 and a maximum value TX2 in the second control state. In the solid line L22 of FIG. 4, the maximum value TX2 in the second control state is a constant value in the range where the rotational speed N of the crank 12 is less than a second speed N2, which is larger than the first speed N1. After reaching the second speed N2, the maximum value TX2 decreases as the rotational speed N of the crank 12 increases. In the double-dashed line L21 and the solid line L22 in FIG. 4, the maximum value TX1 and the maximum value TX2 are equal in the range where the rotational speed N of the crank 12 is greater than or equal to the second speed N2. The maximum value TX2 is increased as the steps of the first ratio R changed during the predetermined period increase in number or as the steps of the first ratio R changed by the signal received during the predetermined period increase in number. In the example of FIG. 4, the controller 42 controls the motor 30 so that the maximum value TX2 with respect to the rotational speed N of the crank 12 becomes the solid line L22 in a case in which the step of the first ratio R changed by the signal received during the predetermined period within the predetermined period is one step in the second control state. The controller 42 controls the motor 30 so that the maximum value TX2 with respect to the rotational speed N of the crank 12 becomes a broken line L23 in a case in which the step of the first ratio R changed by the signal received during the predetermined period within the predetermined period is two steps in the second control state.

In a fourth example, the controller 42 controls the motor 30 in accordance with the human drive force H input to the human-powered vehicle 10. The controller 42 controls the motor 30 so that a maximum value TX of the output of the motor 30 is larger in the second control state than in the first control state. For example, the solid line L22 in FIG. 4 shows an example of the relationship between the rotational speed N of the crank 12 and the maximum value TX1 in the first control state. In the solid line L22 in FIG. 4, the maximum value TX1 in the first control state is a constant value in the range where the rotational speed N of the crank 12 is less than the first speed N1. After reaching the first speed N1, the maximum value TX1 decreases as the rotational speed N of the crank 12 increases. The double-dashed line L21 in FIG. 4 shows an example of the relationship between the rotational speed N of the crank 12 and the maximum value TX2 in the second control state. In the double-dashed line L21 in FIG. 4, the maximum value TX2 in the second control state is a constant value in the range where the rotational speed N of the crank 12 is less than the second speed N2, which is larger than the first speed N1. After reaching the second speed N2, the maximum value TX2 decreases as the rotational speed N of the crank 12 increases. In the double-dashed line L21 and the solid line L22 in FIG. 4, the maximum value TX1 and the maximum value TX2 are equal in the range where the rotational speed N of the crank 12 is greater than or equal to the second speed N2. The maximum value TX2 is decreased as the steps of the first ratio R changed during the predetermined period increase in number or as the steps of the first ratio R changed by the signal received during the predetermined period increase in number. In the example of FIG. 4, the controller 42 controls the motor 30 so that the maximum value TX2 with respect to the rotational speed N of the crank 12 becomes the double-dashed line L21 in a case in which the step of the first ratio R changed by the signal received during the predetermined period within the predetermined period is one step in the second control state. The controller 42 controls the motor 30 so that the maximum value TX2 with respect to the rotational speed N of the crank 12 becomes a broken line L24 in a case in which the step of the first ratio R changed by the signal received during the predetermined period within the predetermined period is two steps in the second control state.

In a fifth example, the controller 42 controls the motor 30 so that a response speed X of the change in the output of the motor 30 with respect to the change in the human drive force H differs between a case in which the human drive force H is increased and a case in which the human drive force H is decreased. The controller 42 can control the motor 30 so that the response speed X differs between the first control state and the second control state. The controller 42 includes a filter processing unit, and the response speed X can be changed by the filter processing unit. Specifically, the controller 42 changes the response speed X by changing a time constant K used by the filter processing unit. The filter processing unit includes, for example, a low pass filter. The response speed X includes a first response speed X1 for a case in which the human drive force H is increased and a second response speed X2 for a case in which the human drive force H is decreased. The first response speed X1 includes a first response speed X11 for the first control state and a first response speed X12 for the second control state. The second response speed X2 includes a second response speed X21 for the first control state and a second response speed X22 for the second control state. The time constant K includes a first time constant K1 for a case in which the human drive force H is increased and a second time constant K2 for a case in which the human drive force H is decreased. The first time constant K1 includes a first time constant K11 for the first control state and a first time constant K12 for the second control state. The second time constant K2 includes a second time constant K21 for the first control state and a second time constant K22 for the second control state.

Figure 5:
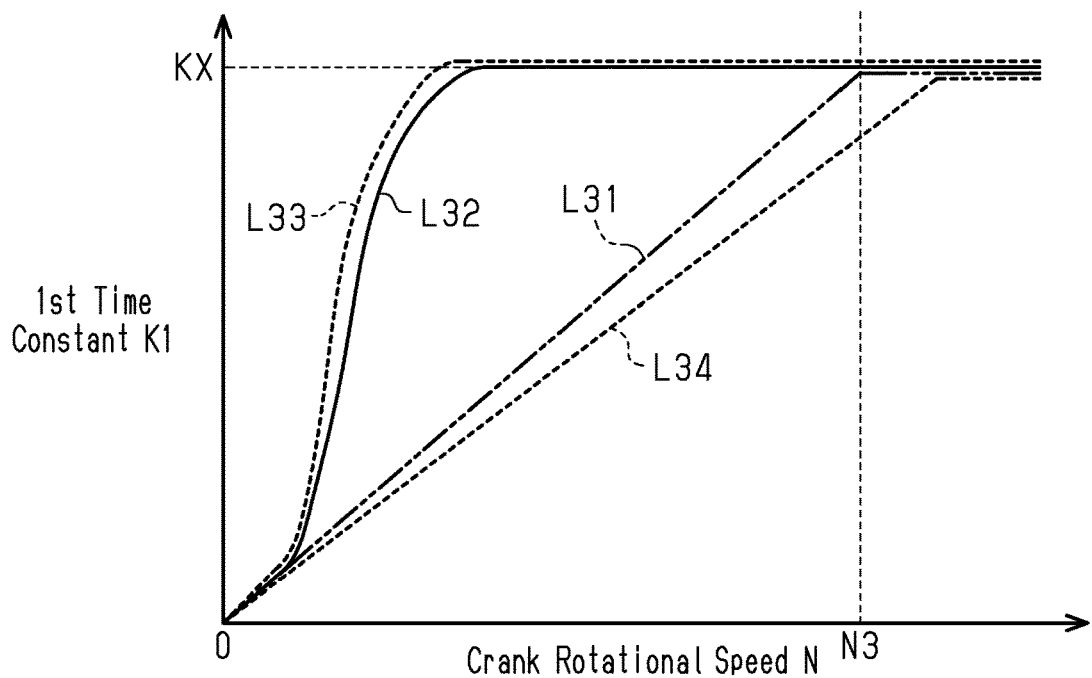
FIG. 5 is a map showing an example of the relationship between the rotational speed of the crank and a first time constant stored in the storage FIG. 2.

The controller 42 controls the motor 30 in accordance with the human drive force H input to the human-powered vehicle 10. The controller 42 controls the motor 30 so that the first response speed X11 of the output of the motor 30 in a case in which the human drive force H is increased in the second control state is higher than the first response speed X12 in the first control state. For example, a double-dashed line L31 in FIG. 5 shows an example of the relationship between the rotational speed N of the crank 12 and the first time constant K11 in the first control state. In the double-dashed line L31 in FIG. 5, the first time constant K11 in the first control state increases as the rotational speed N of the crank 12 increases. In the double-dashed line L31 in FIG. 5, the first time constant K11 in the first control state becomes equal to a first value KX in a case in which the rotational speed N of the crank 12 reaches a third speed N3. Further, the first time constant K11 is maintained at the first value KX at higher than or equal to the third speed N3. A solid line L32 in FIG. 5 shows an example of the relationship between the rotational speed N of the crank 12 and the first time constant K12 in the second control state. In the solid line L32 of FIG. 5, the first time constant K12 in the second control state increases as the rotational speed N of the crank 12 increases. In the solid line L32 of FIG. 5, the first time constant K12 in the second control state becomes equal to the first value KX in a case in which the rotational speed N of the crank 12 reaches the third speed N3. Further, the first time constant K12 is maintained at the first value KX at higher than or equal to the third speed N3. In the example of FIG. 5, the first time constant K11 in the first control state and the first time constant K12 in the second control state are equal in the range where the rotational speed N of the crank 12 is higher than or equal to the third speed N3. Therefore, in the range where the rotational speed N of the crank 12 is higher than or equal to the third speed N3, the first response speed X11 and the first response speed X12 are equal. The controller 42 can determine the first time constant K1 in accordance with the torque TH instead of the rotational speed N of the crank 12 in the first control state and the second control state. In this case, the relationship in which the rotational speed N of the crank 12 in FIG. 5 is replaced by the torque TH can be the relationship between the torque TH and the first time constant K1 in the first control state and the second control state. Preferably, the first response speed X12 is increased as the steps of the first ratio R changed during the predetermined period increase in number or as the steps of the first ratio R changed by the signal received during the predetermined period increase in number. In the example of FIG. 5, the controller 42 controls the motor 30 so that the first time constant K12 with respect to the rotational speed N of the crank 12 becomes the solid line L32 in a case in which the step of the first ratio R changed by the signal received during the predetermined period within the predetermined period is one step in the second control state. The controller 42 controls the motor 30 so that the first time constant K12 with respect to the rotational speed N of the crank 12 becomes a broken line L33 in a case in which the first ratio R is changed by two steps by the signal received during the predetermined period in the second control state.

Figure 6:
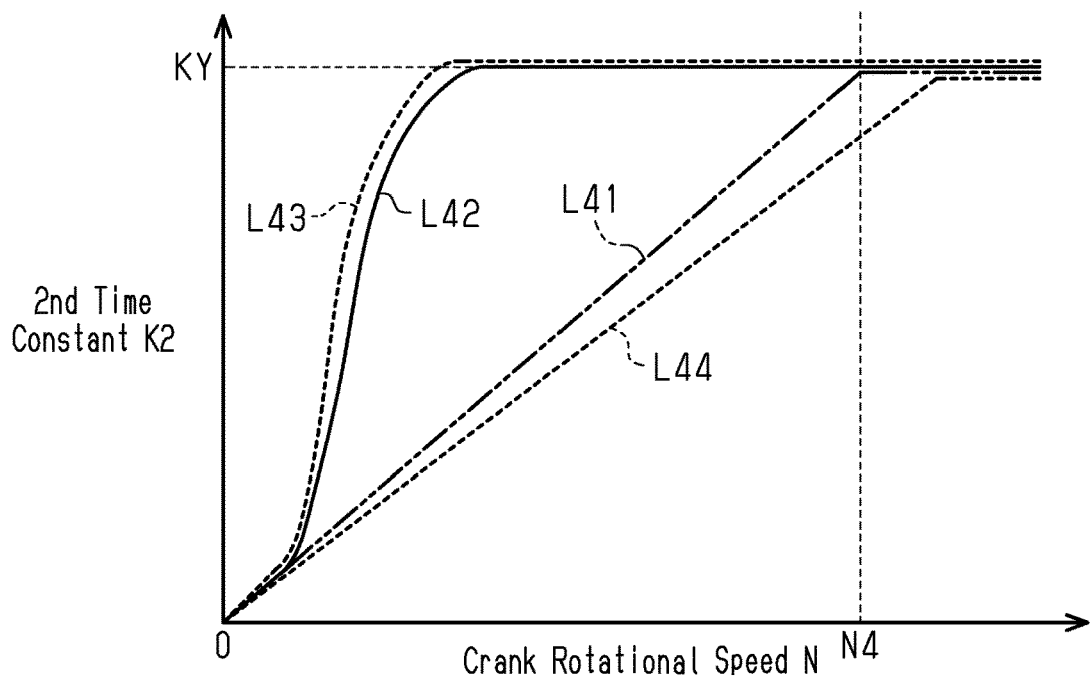
FIG. 6 is a map showing an example of the relationship between the rotational speed of the crank and a second time constant stored in the storage of FIG. 2.

The controller 42 controls the motor 30 in accordance with the human drive force H input to the human-powered vehicle 10. The controller 42 controls the motor 30 so that the second response speed X22 of the output of the motor 30 in a case in which the human drive force H is decreased in the second control state is preferably higher than the second response speed X21 in the first control state. For example, a double-dashed line L41 in FIG. 6 shows an example of the relationship between the rotational speed N of the crank 12 and the second time constant K21 in the first control state. In the double-dashed line L41 of FIG. 6, the second time constant K21 in the first control state increases as the rotational speed N of the crank 12 increases. In the double-dashed line L41 in FIG. 6, the second time constant K21 in the first control state becomes a second value KY in a case in which the rotational speed N of the crank 12 reaches a fourth speed N4. Further, the second time constant K21 is maintained at the second value KY at higher than or equal to the fourth speed N4. A solid line L42 in FIG. 6 shows an example of the relationship between the rotational speed N of the crank 12 and the second time constant K22 in the second control state. In the solid line L42 in FIG. 6, the second time constant K22 in the second control state increases as the rotational speed N of the crank 12 increases. In the solid line L42 in FIG. 6, the second time constant K22 in the second control state becomes equal to the second value KY in a case in which the rotational speed N of the crank 12 reaches the fourth speed N4. Further, the second time constant K22 is maintained at the second value KY at higher than or equal to the fourth speed N4. In the example of FIG. 6, the second time constant K21 in the first control state and the second time constant K22 in the second control state are equal in the range where the rotational speed N of the crank 12 is higher than or equal to the fourth speed N4. Therefore, in the range where the rotational speed N of the crank 12 is higher than or equal to the fourth speed N4, the first response speed X11 and the first response speed X12 are equal. The controller 42 can determine the second time constant K2 in accordance with the torque TH instead of the rotational speed N of the crank 12 in the first control state and the second control state. In this case, the relationship in which the rotational speed N of the crank 12 in FIG. 6 is replaced by the torque TH can be the relationship between the torque TH and the first time constant K in the first control state and the second control state. Preferably, the second response speed X2 is increased as the steps of the first ratio R changed during the predetermined period increase in number or as the steps of the first ratio R changed by the signal received during the predetermined period increase in number. In the example of FIG. 6, the controller 42 controls the motor 30 so that the second time constant K22 with respect to the rotational speed N of the crank 12 becomes the solid line L42 in a case in which the step of the first ratio R changed by the signal received during the predetermined period within the predetermined period is one step in the second control state. The controller 42 controls the motor 30 so that the second time constant K22 with respect to the rotational speed N of the crank 12 becomes a broken line L43 in a case in which the step of the first ratio R changed by the signal received during the predetermined period within the predetermined period is two steps in the second control state.

The relationship between the rotational speed N of the crank 12 and the first time constant K1 can be equal to the relationship between the rotational speed N of the crank 12 and the second time constant K2. Specifically, the line shape and the corresponding numerical values of the double-dashed line L31 in FIG. 5 can be the same as those of the double-dashed line L41 in FIG. 6, and the line shape and the corresponding numerical values of the solid line L32 in FIG. 5 can be the same as those of the solid line L42 in FIG. 6. The relationship between the rotational speed N of the crank 12 and the first time constant K1 can differs from the relationship between the rotational speed N of the crank 12 and the second time constant K2. For example, the line shape of at least one of the lines L31 to L34 in FIG. 5 differs from the line shape of the lines L41 to L44 in FIG. 6. Furthermore, the controller 42 can control the motor 30 so that one of the first response speed X1 and the second response speed X2 is the same in the first control state and the second control state. Moreover, the controller 42 can control the motor 30 so that one of the first response speed X1 and the second response speed X2 in the second control state is lower than one of the first response speed X1 and the second response speed X2 in the first control state.

The controller 42 can execute the control of only one of the three examples of one of the first example and the second example, one of the third example and the fourth example, and the fifth example. The controller 42 can execute the control of two or three of the three examples of one of the first example and the second example, one of the third example and the fourth example, and the fifth example.

Preferably, the controller 42 changes a control state of the motor 30 from a third control state to a fourth control state that differs from the third control state in at least one of a case in which the first ratio R is changed by the transmission 34 and a case in which a signal for changing the first ratio R is received. Further, the controller 42 changes the control state of the motor 30 from the fourth control state to a fifth control state that differs from the fourth control state in accordance with a value related to at least one of a vehicle speed V of the human-powered vehicle 10, the human drive force H, an inclination angle G of the human-powered vehicle, and a state of a rider of the human-powered vehicle 10.

The fourth control state includes a first control state and a second control state that differs from the first control state. Preferably, the controller 42 controls the motor 30 in the first control state in at least one of a case in which the first ratio R is decreased and changed by only one step during the predetermined period and a case in which a signal is received for decreasing and changing the first ratio R by one step during the predetermined period. Preferably, the controller 42 controls the motor 30 in the second control state in at least one of a case in which the first ratio R is decreased and changed by two or more steps during the predetermined period and a case in which a signal is received for decreasing and changing the first ratio R by two or more steps during the predetermined period.

The fourth control state includes a first control state and a second control state that differs from the first control state. Preferably, the controller 42 controls the motor 30 in the first control state in at least one of a case in which the first ratio R is increased and changed by only one step during the predetermined period and a case in which a signal for increasing and changing the first ratio R by one step is received during the predetermined period. Preferably, the controller 42 controls the motor 30 in the second control state in at least one of a case in which the first ratio R is increased and changed by two or more steps during the predetermined period and a case in which a signal for increasing and changing the first ratio R by two or more steps is received during the predetermined period.

The fifth control state includes a third control state. The controller 42 changes the control state of the motor 30 from the third control state to the first control state or the second control state in at least one of a case in which the first ratio R is changed by the transmission 34 and a case in which a signal for changing the first ratio R is received. After the controller 42 changes the control state of the motor from the third control state to the first control state or the second control state, the controller 42 changes the control state of the motor 30 from the first control state or the second control state to the third control state in accordance with the value related to at least one of the vehicle speed V of the human-powered vehicle 10, the human drive force H, the inclination angle G of the human-powered vehicle 10, and the state of the rider of the human-powered vehicle 10. In the third control state, the controller 42 controls the motor 30 in accordance with the human drive force H.

Preferably, the controller 42 controls the motor 30 so that the second ratio A4 of an assist force produced by the motor 30 to the human drive force H in the fourth control state is larger than the second ratio A3 in the third control state. In the first example, the second ratio A4 in the fourth control state corresponds to the second ratio A2 in the second control state, and the second ratio A3 in the third control state corresponds to the second ratio A1 in the first control state. Preferably, the second ratio A4 is increased as the steps of the first ratio R changed during the predetermined period increase in number or as the steps of the first ratio R changed by the signal received during the predetermined period increase in number.

Preferably, the controller 42 controls the motor 30 so that the second ratio A4 of the assist force produced by the motor 30 to the human drive force H in the fourth control state is smaller than the second ratio A3 in the third control state. In the second example, the second ratio A4 in the fourth control state corresponds to the second ratio A2 in the second control state, and the second ratio A3 in the third control state corresponds to the second ratio A1 in the first control state. Preferably, the second ratio A4 is increased as the steps of the first ratio R changed during the predetermined period increase in number or as the steps of the first ratio R changed by the signal received during the predetermined period increase in number.

Preferably, the controller 42 controls the motor 30 so that a maximum value TX of the output of the motor 30 is larger in the fourth control state than in the third control state. In the third example, the maximum value TX4 of the output of the motor 30 in the fourth control state corresponds to the maximum value TX2 of the output of the motor 30 in the second control state, and the maximum value TX3 of the output of the motor 30 in the third control state corresponds to the maximum value TX1 of the output of the motor 30 in the first control state. The maximum value TX4 is preferably increased as the steps of the first ratio R changed during the predetermined period increase in number or as the steps of the first ratio R changed by the signal received during the predetermined period increase in number.

Preferably, the controller 42 controls the motor 30 so that a maximum value TX of the output of the motor 30 is smaller in the fourth control state than in the third control state. In the fourth example, the maximum value TX4 of the output of the motor 30 in the fourth control state corresponds to the maximum value TX2 of the output of the motor 30 in the second control state, and the maximum value TX3 of the output of the motor 30 in the third control state corresponds to the maximum value TX1 of the output of the motor 30 in the first control state. Preferably, the maximum value TX3 is decreased as the steps of the first ratio R changed during the predetermined period increase in number or as the steps of the first ratio R changed by the signal received during the predetermined period increase in number.

Preferably, the controller 42 controls the motor 30 so that the first response speed X1 of the output of the motor 30 in a case in which the human drive force H is increased in the fourth control state is higher than the first response speed X1 in the third control state. In the fifth example, the first response speed X14 in the fourth control state corresponds to the first response speed X12 in the second control state, and the first response speed X13 in the third control state corresponds to the first response speed X11 in the first control state. Preferably, the first response speed X14 is increased as the steps of the first ratio R changed during the predetermined period increase in number or as the steps of the first ratio R changed by the signal received during the predetermined period increase in number.

Preferably, the controller 42 controls the motor 30 so that the second response speed X2 of the output of the motor 30 in a case in which the human drive force H is decreased in the fourth control state is higher than the second response speed X2 in the third control state. In the fifth example, the second response speed X24 in the fourth control state corresponds to the second response speed X22 in the second control state. The second response speed X23 in the third control state corresponds to the second response speed X21 in the first control state. Preferably, the second response speed X24 is increased as the steps of the first ratio R changed during the predetermined period increase in number or as the steps of the first ratio R changed by the signal received during the predetermined period increase in number.

A process for changing the control state from the third control state to the first control state or the second control state will now be described with reference to FIG. 7. In a case in which power is supplied from the battery 28 to the controller 42, the controller 42 starts the process and proceeds to step S11 of the flowchart shown in FIG. 7. As long as power is supplied, the controller 42 executes the process from step S11 in predetermined cycles.

In step S11, the controller 42 determines whether or not in the motor 30 is controlled in the third control state. In a case in which the controller 42 is not controlling the motor 30 in the third control state, the controller 42 terminates the process. In a case in which the controller 42 is controlling the motor 30 in the third control state, the controller 42 proceeds to step S12.

In step S12, the controller 42 determines whether or not to change the first ratio R by one step. Specifically, the controller 42 determines to change the first ratio R by one step in a case in which the first ratio R is changed by only one step during a predetermined period or a case in which a signal for changing the first ratio R by one step is received during the predetermined period. In a case in which the controller 42 changes the first ratio R by one step, the controller 42 proceeds to step S13. In step S13, the controller 42 controls the motor 30 in the first control state and terminates the process. Since the fourth control state includes the first control state and the second control state, the controller 42 controls the motor 30 in the fourth control state in step S13 and then terminates the process.

In a case in which the controller 42 determines not to change the first ratio R by one step in step S12, the controller 42 proceeds to step S14. In step S14, the controller 42 determines whether or not to change the first ratio R by two or more steps. Specifically, the controller 42 determines to change the first ratio R by two or more steps in a case in which the first ratio R is decreased and changed by two or more steps during a predetermined period and a case in which a signal for decreasing and changing the first ratio R by two or more steps is received during the predetermined period. In a case in which the controller 42 does not change the first ratio R by two or more steps, the controller 42 terminates the process. In a case in which the controller 42 changes the first ratio R by two or more steps, the controller 42 proceeds to step S15. In step S15, the controller 42 controls the motor 30 in the second control state and then terminates the process. Since the fourth control state includes the first control state and the second control state, the controller 42 controls the motor 30 in the fourth control state in step S15 and then terminates the process.

The controller 42 preferably changes the control state of the motor 30 from the fourth control state to the fifth control state in a case in which an increased amount DV of a value related to a vehicle speed V becomes greater than or equal to a predetermined first value DV1 or in a case in which a value related to the vehicle speed V becomes greater than or equal to a predetermined second value VA in the fourth control state. The controller 42 returns the control state of the motor 30 from the fourth control state to the third control state in a case in which the increased amount DV of a value related to the vehicle speed V becomes greater than or equal to the predetermined first value DV1 or in a case in which a value related to the vehicle speed V becomes greater than or equal to the predetermined second value VA in the fourth control state. The controller 42 returns the control state of the motor 30 from the first control state or the second control state to the third control state in a case in which the increased amount DV of a value related to the vehicle speed V becomes greater than or equal to the predetermined first value DV1 or in a case in which a value related to the vehicle speed V becomes greater than or equal to the predetermined second value VA in the first control state or the second control state. The increased amount DV of the value related to the vehicle speed V includes an increased amount of the vehicle speed V. The increased amount of the vehicle speed V can be acceleration. The value related to the vehicle speed V includes the vehicle speed V. The value related to the vehicle speed V can be the rotational speed of the drive wheel 14.

A process for changing the control state from the fourth control state to the fifth control state in accordance with the vehicle speed V will now be described with reference to FIG. 8. In a case in which power is supplied from the battery 28 to the controller 42, the controller 42 starts the process and proceeds to step S21 of the flowchart shown in FIG. 8. As long as power is supplied, the controller 42 executes the process from step S21 in predetermined cycles.

In step S21, the controller 42 determines whether or not the motor 30 is controlled in the fourth control state. In a case in which the controller 42 is not controlling the motor 30 in the fourth control state, the controller 42 terminates the process. In a case in which the controller 42 is controlling the motor 30 in the fourth control state in step S21, the controller 42 proceeds to step S22.

In step S22, the controller 42 determines whether or not the increased amount DV of a value related to the vehicle speed V has become greater than or equal to the predetermined first value DV1 or whether or not the value related to the vehicle speed V has become greater than or equal to the predetermined second value VA. In a case in which the increased amount DV of the value related to the vehicle speed V has not become greater than or equal to the predetermined first value DV1 and the value related to the vehicle speed V has not become greater than or equal to the predetermined second value VA, the controller 42 terminates the process. In a case in which the increased amount DV of the value related to the vehicle speed V has become greater than or equal to the predetermined first value DV1 or the value related to the vehicle speed V has become greater than or equal to the predetermined second value VA, the controller 42 proceeds to step S23. In step S23, the controller 42 changes the control state to the fifth control state and terminates the process. The fifth control state includes the third control state. Thus, subsequent to step S23, the controller 42 controls the motor 30 to return to the state before changing to the fourth control state.

The controller 42 can change the control state of the motor 30 from the fourth control state to the fifth control state in accordance with at least one of the human drive force H, the inclination angle G, and the state of the rider in place of or in addition to the vehicle speed V.

In a case in which the human drive force H is used, the controller 42 preferably changes the control state of the motor 30 from the fourth control state to the fifth control state in a case in which a decreased amount DH of a value related to the human drive force H becomes greater than or equal to a predetermined third value DH1 or in a case in which a value related to the human drive force H becomes less than or equal to a predetermined fourth value HA in the fourth control state. The controller 42 returns the control state of the motor 30 from the fourth control state to the third control state in a case in which the decreased amount DH of a value related to the human drive force H becomes greater than or equal to the predetermined third value DH1 in the fourth control state or in a case in which a value related to the human drive force H becomes less than or equal to the predetermined fourth value HA in the fourth control state. The controller 42 returns the control state of the motor 30 from the first control state or the second control state to the third control state or in a case in which the decreased amount DH of a value related to the human drive force H becomes greater than or equal to the predetermined third value DH1 or in a case in which a value related to the human drive force H becomes less than or equal to the predetermined fourth value HA in the first control state or the second control state. The decreased amount DH of the value related to the human drive force H includes an increased amount of the human drive force H. The value related to the human drive force H includes the human drive force H. The value related to the human drive force H can be the torque of the human drive force H or the power of the human drive force H.

Figure 8:
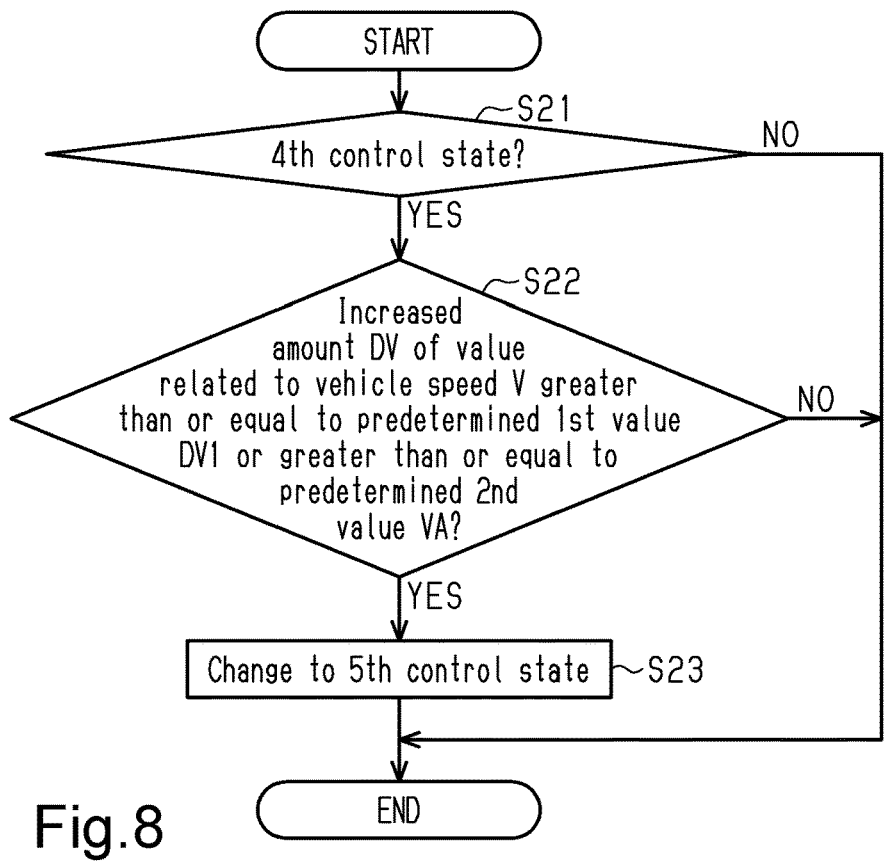
FIG. 8 is a flowchart of a control process for switching from a fourth control state to a fifth control state in accordance with a vehicle speed executed by the electronic controller of FIG. 2.
Figure 9:
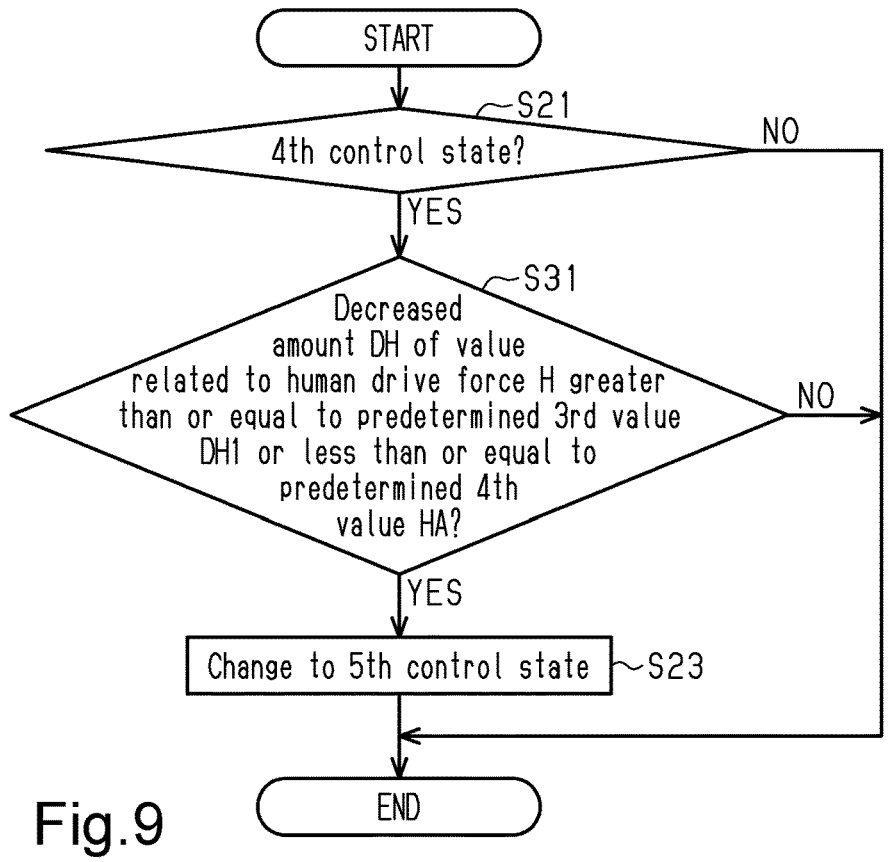
FIG. 9 is a flowchart of a control process for switching from the fourth control state to the fifth control state in accordance with a human drive force executed by the electronic controller of FIG. 2.

In a case in which the human drive force H is used instead of the vehicle speed V, the controller 42, for example, executes step S31 instead of step S21 of FIG. 8 as shown in FIG. 9. If an affirmative determination is given in step S21, the controller 42 proceeds to step S31. In step S31, the controller 42 determines whether or not the decreased amount DH of a value related to the human drive force H is greater than or equal to a predetermined third value DH1 or a value related to the human drive force H is less than or equal to a predetermined fourth value HA. In a case in which the decreased amount DH of a value related to the human drive force H is greater than or equal to the predetermined third value DH1 or a value related to the human drive force H is less than or equal to the predetermined fourth value HA, the controller 42 proceeds to step S23.

In a case in which the inclination angle G is used, the controller 42 preferably changes the control state of the motor 30 from the fourth control state to the fifth control state in a case in which a decreased amount DG of a value related to the inclination angle G of the human-powered vehicle 10 becomes greater than or equal to a predetermined fifth value DGA or in a case in which a value related to the inclination angle G of the human-powered vehicle 10 becomes less than or equal to a predetermined sixth value in the fourth control state. The controller 42 returns the control state of the motor 30 from the fourth control state to the third control state in a case in which the decreased amount DG of a value related to the inclination angle G becomes greater than or equal to the predetermined fifth value DGA or in a case in which a value related to the inclination angle G becomes less than or equal to the predetermined sixth value GA in the fourth control state. The controller 42 returns the control state of the motor 30 from the first control state or the second control state to the third control state in a case in which the decreased amount DG of a value related to the inclination angle G becomes greater than or equal to the predetermined fifth value DGA or in a case in which a value related to the inclination angle G becomes less than or equal to the predetermined sixth value GA in the first control state and the second control state. The decreased amount DG of the value related to the inclination angle G includes the decreased amount of the inclination angle G. The value related to the inclination angle G includes the inclination angle G. The inclination angle G is preferably a pitch angle of the human-powered vehicle 10. The inclination angle G can be the inclination angle of the road surface on which the human-powered vehicle 10 travels.

Figure 10:
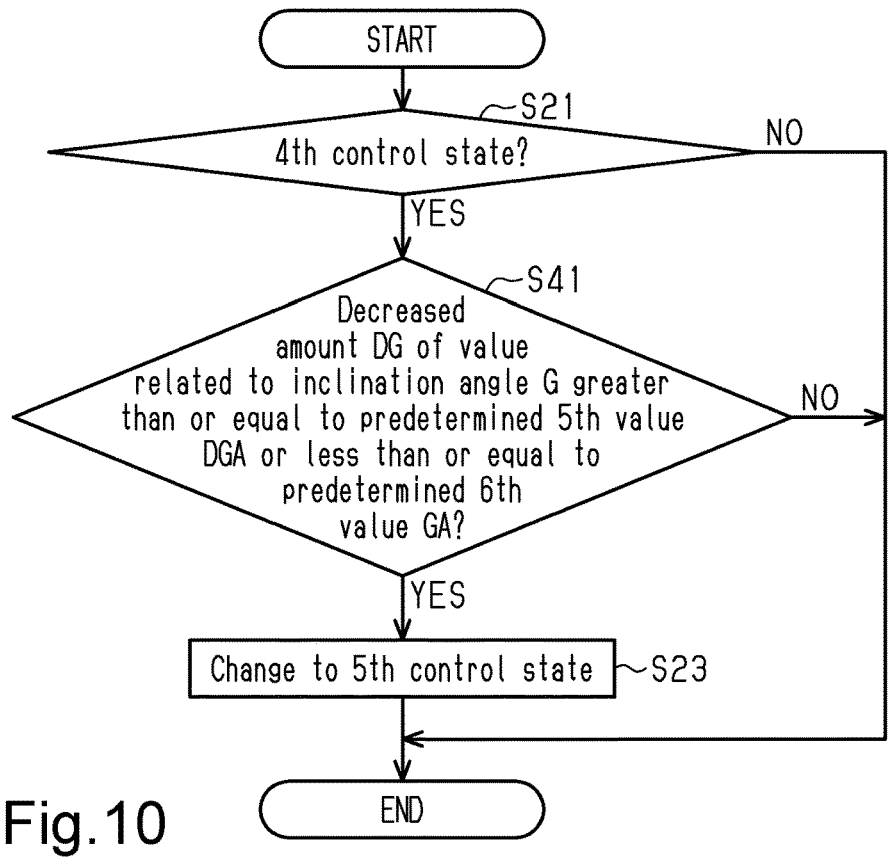
FIG. 10 is a flowchart of a control process for switching from the fourth control state to the fifth control state in accordance with an inclination angle executed by the electronic controller of FIG. 2.

In a case in which the inclination angle D is used instead of the vehicle speed V, the controller 42, for example, executes step S41 instead of step S21 of FIG. 8 as shown in FIG. 10. If an affirmative determination is given in step S21, the controller 42 proceeds to step S41. In step S41, the controller 42 determines whether or not the decreased amount DG of a value related to the inclination angle G is greater than or equal to the predetermined fifth value DGA or a value related to the inclination angle G is less than or equal to a predetermined sixth value GA. In a case in which the decreased amount DG of the value related to the inclination angle G has become greater than or equal to the predetermined fifth value DGA or in a case in which the value related to the inclination angle G has become less than or equal to the predetermined sixth value GA, the controller 42 proceeds to step S23.

In a case in which the state of the rider is used, the state of the rider of the human-powered vehicle 10 can preferably include the heart rate M of the rider. The controller 42 changes the control state of the motor 30 from the fourth control state to the fifth control state in a case in which a decreased amount DM of a value related to the heart rate M becomes greater than or equal to a predetermined seventh value DMA or in a case in which a value related to the heart rate M of the rider becomes less than or equal to a predetermined eighth value MA in the fourth control state. The controller 42 returns the control state of the motor 30 from the fourth control state to the third control state in a case in which a decreased amount DM of a value related to the heart rate M becomes greater than or equal to the predetermined seventh value DMA or in a case in which a value related to the heart rate M of the rider becomes less than or equal to a predetermined eighth value MA in the fourth control state. The controller 42 returns the control state of the motor 30 from the first control state or the second control state to the third control state in a case in which the decreased amount DM of a value related to the heart rate M becomes greater than or equal to the predetermined seventh value DMA or in a case in which a value related to the heart rate M of the rider becomes less than or equal to the predetermined eighth value MA in the first control state or the second control state. The decreased amount DM of the value related to the heart rate M includes a decreased amount of the heart rate M. The value related to the heart rate M includes the heart rate M. The value related to the heart rate M can be a pulse.

Figure 11:
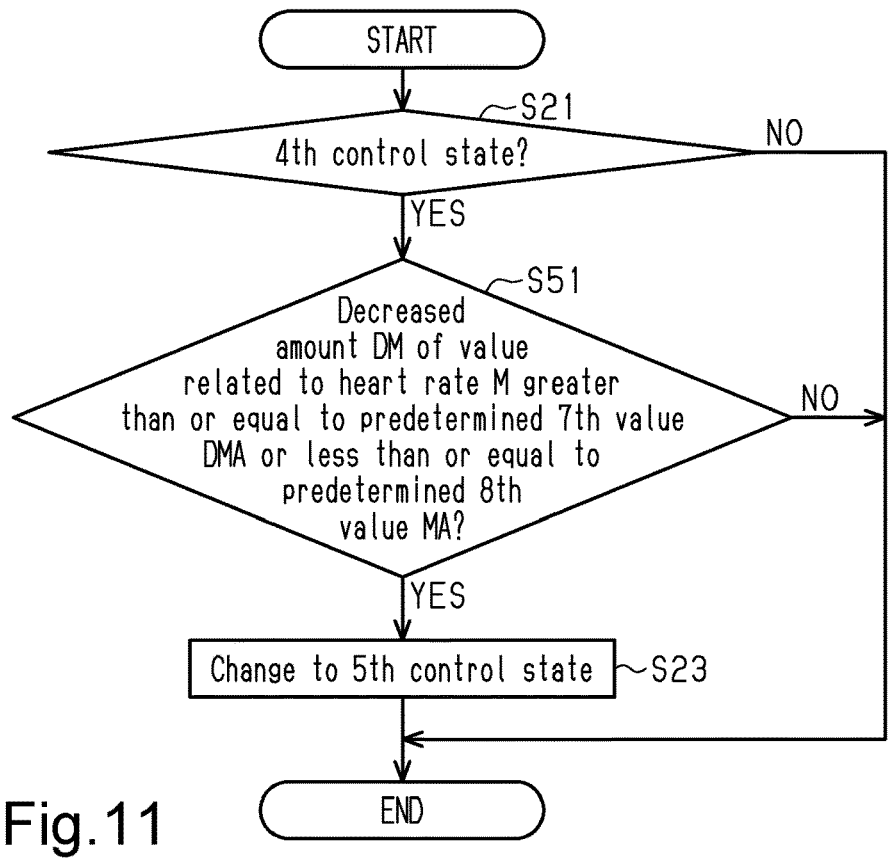
FIG. 11 is a flowchart of a control process for switching from the fourth control state to the fifth control state in accordance with a heart rate executed by the electronic controller of FIG. 2.

In a case in which the state of the rider is used instead of the vehicle speed V, the controller 42 executes, for example, step S51 instead of step S21 of FIG. 8 as shown in FIG. 11. If an affirmative determination is given in step S21, the controller 42 proceeds to step S51. In step S51, the controller 42 determines whether or not the decreased amount DM of a value related to the heart rate M is greater than or equal to the predetermined seventh value DMA or a value related to the heart rate M is less than or equal to the predetermined eighth value MA. In a case in which the decreased amount DM of the value related to the heart rate M has become greater than or equal to the predetermined seventh value DMA or in a case in which the value related to the heart rate M has become less than or equal to the predetermined eighth value MA, the controller 42 proceeds to step S23.

In a case in which the control state of the motor 30 is changed from the fourth control state to the fifth control state in accordance with at least one of the vehicle speed V, the human drive force H, the inclination angle G, and the state of the rider, the controller 42 changes the control state from the fourth control state to the fifth control state if the determination of at least one of step S22 in FIG. 8, step S31 in FIG. 9, step S41 in FIG. 10 and step S51 in FIG. 11 is YES.

Modifications

The description related with the above embodiment exemplifies, without any intention to limit, an applicable form of a human-powered vehicle control device in accordance with the present disclosure. In addition to the embodiment described above, the human-powered vehicle control device in accordance with the present disclosure is applicable to, for example, modifications of the above embodiment that are described below and combinations of at least two of the modifications that do not contradict each other. In the modifications described hereafter, same reference numerals are given to those components that are the same as the corresponding components of the above embodiment. Such components will not be described in detail.

The controller 42 can control the motor 30 in accordance with the change amount of the first ratio R instead of the number of steps of the first ratio R. In this case, the transmission 34 includes a continuously variable transmission, and the transmission 34 can be configured to change the first ratio R of the rotational speed of the drive wheel 14 to the rotational speed of the rotary body to which the human drive force H is input in a stepless manner. The controller 42 controls the motor 30 in the first control state in at least one of a case in which the first ratio R is changed so that a change amount DR of the first ratio R in a predetermined period becomes less than or equal to a first change amount DR1 and a case in which a signal for changing the first ratio R is received so that a change amount DR of the first ratio R in the predetermined period becomes less than or equal to the first change amount DR1. The controller 42 controls the motor 30 in the second control state that differs from the first control state in at least one of a case in which the first ratio R is changed so that the change amount DR of the first ratio R in a predetermined period exceeds the first change amount DR1 and a case in which a signal is received for changing the first ratio R so that the change amount DR of the first ratio R in the predetermined period exceeds the first change amount DR1. In this case, in the first example of the first embodiment, the second ratio A4 in the fourth control state is increased as the change amount of the first ratio R changed during a predetermined period or the change amount of the first ratio R changed by the signal received during the predetermined period increases. In the second example of the first embodiment, the second ratio A4 in the fourth control state is decreased as the change amount of the first ratio R changed during a predetermined period or the change amount of the first ratio R changed by the signal received during the predetermined period increases. In the third example of the first embodiment, the maximum value TX4 in the fourth control state is increased as the change amount of the first ratio R changed during a predetermined period or the change amount of the first ratio R changed by the signal received during the predetermined period increases. In the fourth example of the first embodiment, the maximum value TX4 in the fourth control state is decreased as the change amount of the first ratio R changed during a predetermined period or the change amount of the first ratio R changed by the signal received during the predetermined period increases. In the fifth example of the first embodiment, the first response speed X14 in the fourth control state is increased as the change amount of the first ratio R changed during the predetermined period or the change amount of the first ratio R changed by the signal received during the predetermined period increases. In the fifth example of the first embodiment, the second response speed X24 in the fourth control state is increased as the change amount of the first ratio R changed during the predetermined period or the change amount of the first ratio R changed by the signal received during the predetermined period increases.

Figure 7:
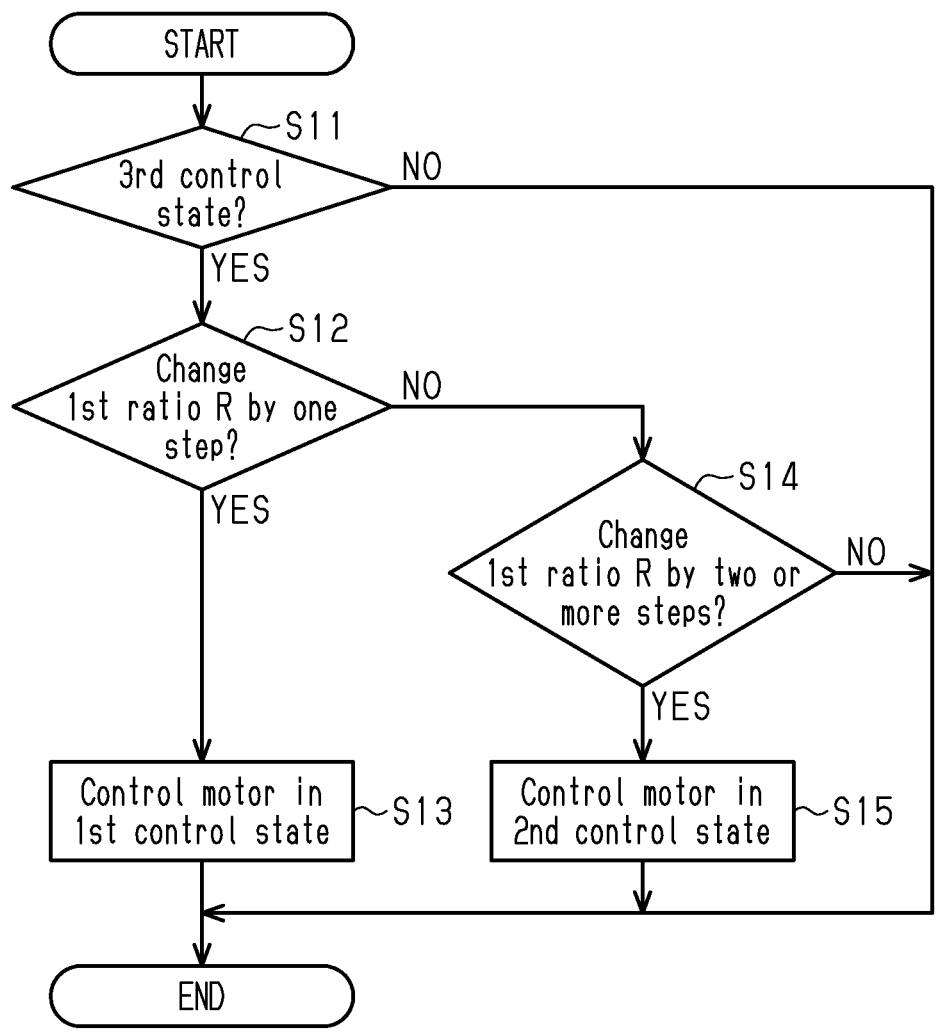
FIG. 7 is a flowchart of a control process for switching a first control state and a second control state executed by the electronic controller of FIG. 2.
Figure 12:
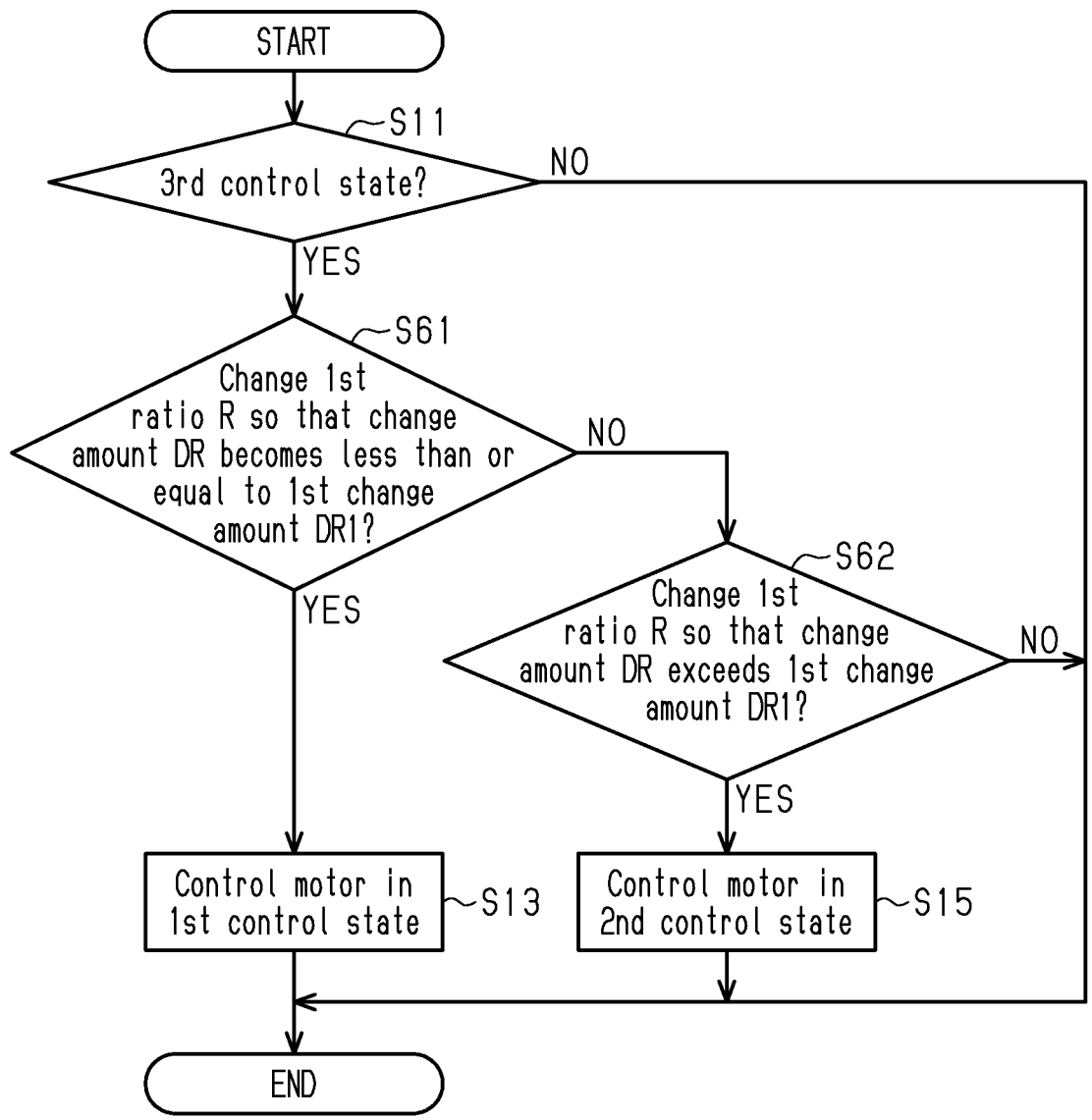
FIG. 12 is a flowchart of a modified control process for switching a first control state and a second control state executed by the electronic controller of FIG. 2.

In this case, the controller 42 executes step S61 of FIG. 12 instead of step S12 of FIG. 7. Further, the controller 42 executes step S62 of FIG. 12 instead of step S12 of FIG. 7. More specifically, in a case in which the controller 42 is controlling the motor 30 in the third control state in step S11, the controller 42 proceeds to step S61.

In step S61, the controller 42 determines whether or not to change the first ratio R so that the change amount DR becomes less than or equal to the first change amount DR1. Specifically, the controller 42 determines to change the first ratio R so that the change amount DR becomes less than or equal to the first change amount DR1 in a case in which the first ratio R is changed such that the change amount DR of the first ratio R during the predetermined period becomes less than or equal to the first change amount DR1 or a case in which a signal is received for changing the first ratio R such that the change amount DR of the first ratio R during the predetermined period becomes less than or equal to the first change amount DR1. The controller 42 proceeds to step S13 to change the first ratio R so that the change amount DR becomes less than or equal to the first change amount DR1.

In a case in which the controller 42 determines not to change the first ratio R so that the change amount DR does not become less than or equal to the first change amount DR1 in step S61, the controller 42 proceeds to step S62. In step S62, the controller 42 determines whether or not to change the first ratio R so that the change amount DR exceeds the first change amount DR1. Specifically, the controller 42 determines to change the first ratio R so that the change amount DR exceeds the first change amount DR1 in a case in which the first ratio R is changed such that the change amount DR of the first ratio R during the predetermined period exceeds the first change amount DR1 or a case in which a signal is received for changing the first ratio R such that the change amount DR of the first ratio R during the predetermined period exceeds the first change amount DR1. In a case of not changing the first ratio R so that the change amount DR exceeds the first change amount DR1, the controller 42 terminates the process. The controller 42 proceeds to step S15 to change the first ratio R so that the change amount DR exceeds the first change amount DR1. The phrase "at least one of" as used in this disclosure means "one or more" of a desired choice. For one example, the phrase "at least one of" as used in this disclosure means "only one single choice" or "both of two choices" if the number of its choices is two. For other example, the phrase "at least one of" as used in this disclosure means "only one single choice" or "any combination of equal to or more than two choices" if the number of its choices is equal to or more than three.

What is claimed is:

1. A human-powered vehicle control device comprising:
   an electronic controller configured to control a motor that assists in propulsion of a human-powered vehicle including a transmission configured to change, in steps, a first ratio of a rotational speed of a drive wheel to a rotational speed of a rotary body to which human drive force is input,
   the electronic controller being configured to control the motor in a first control state in at least one of a case in which the first ratio is changed by only one step during a predetermined period and a case in which a signal is received for changing the first ratio by one step during the predetermined period, and
   the electronic controller being configured to control the motor in a second control state that differs from the first control state in at least one of a case in which the first ratio is changed by two or more steps during the predetermined period and a case in which a signal is received for changing the first ratio by two at least steps during the predetermined period.

2. The human-powered vehicle control device according to claim 1, wherein
   the electronic controller is configured to control the motor in accordance with the human drive force input to the human-powered vehicle, and
   the electronic controller is configured to control the motor so that a second ratio of an assist force produced by the motor to the human drive force in the second control state is larger than the second ratio in the first control state.

3. The human-powered vehicle control device according to claim 2, wherein
   the second ratio is increased as the steps of the first ratio changed during the predetermined period increase in number or as the steps of the first ratio changed by the signal received during the predetermined period increase in number.

4. The human-powered vehicle control device according to claim 1, wherein
   the electronic controller is configured to control the motor in accordance with the human drive force input to the human-powered vehicle, and
   the electronic controller is configured to control the motor so that a second ratio of an assist force produced by the motor to the human drive force in the second control state is smaller than the second ratio in the first control state.

5. The human-powered vehicle control device according to claim 4, wherein
   the second ratio is decreased as the steps of the first ratio changed during the predetermined period increase in number or as the steps of the first ratio changed by the signal received during the predetermined period increase in number.

6. The human-powered vehicle control device according to claim 1, wherein
   the electronic controller is configured to control the motor in accordance with the human drive force input to the human-powered vehicle, and the electronic controller controls the motor so that a maximum value of an output of the motor is larger in the second control state than in the first control state.

7. The human-powered vehicle control device according to claim 6, wherein
the maximum value is increased as the steps of the first ratio changed during the predetermined period increase in number or as the steps of the first ratio changed by the signal received during the predetermined period increase in number.

8. The human-powered vehicle control device according to claim 1, wherein
the electronic controller is configured to control the motor in accordance with the human drive force input to the human-powered vehicle, and
the electronic controller is configured to control the motor so that a maximum value of an output of the motor is smaller in the second control state than in the first control state.

9. The human-powered vehicle control device according to claim 8, wherein
the maximum value is decreased as the steps of the first ratio changed during the predetermined period increase in number or as the steps of the first ratio changed by the signal received during the predetermined period increase in number.

10. The human-powered vehicle control device according to claim 1, wherein
the electronic controller is configured to control the motor in accordance with the human drive force input to the human-powered vehicle, and
the electronic controller is configured to control the motor so that a first response speed of an output of the motor in a case in which the human drive force is increased in the second control state is higher than the first response speed in the first control state.

11. The human-powered vehicle control device according to claim 10, wherein
the first response speed is increased as the steps of the first ratio changed during the predetermined period increase in number or as the steps of the first ratio changed by the signal received during the predetermined period increase in number.

12. The human-powered vehicle control device according to claim 1, wherein
the electronic controller is configured to control the motor in accordance with the human drive force input to the human-powered vehicle, and
the electronic controller is configured to control the motor so that a second response speed of an output of the motor in a case in which the human drive force is decreased in the second control state is higher than the second response speed in the first control state.

13. The human-powered vehicle control device according to claim 12, wherein
the second response speed is increased as the steps of the first ratio changed during the predetermined period increase in number or as the steps of the first ratio changed by the signal received during the predetermined period increase in number.

14. The human-powered vehicle control device according to claim 1, wherein
the electronic controller is configured to control the motor in the first control state in at least one of a case in which the first ratio is decreased and changed by only one step during the predetermined period and a case in which a signal is received for decreasing and changing the first ratio by one step during the predetermined period, and
the electronic controller is configured to control the motor in the second control state in at least one of a case in which the first ratio is decreased and changed by at least two steps during the predetermined period and a case in which a signal is received for decreasing and changing the first ratio by at least two steps during the predetermined period.

15. The human-powered vehicle control device according to claim 1, wherein
the electronic controller is configured to control the motor in the first control state in at least one of a case in which the first ratio is increased and changed by only one step during the predetermined period and a case in which a signal is received for increasing and changing the first ratio by one step during the predetermined period, and
the electronic controller is configured to control the motor in the second control state in at least one of a case in which the first ratio is increased and changed by at least two steps during the predetermined period and a case in which a signal is received for increasing and changing the first ratio by at least two steps during the predetermined period.

16. The human-powered vehicle control device according to claim 1, wherein
the state of the rider of the human-powered vehicle includes a heart rate of the rider, and
the electronic controller is configured to change the control state of the motor from the fourth control state to the fifth control state in a case in which a decreased amount of a value related to the heart rate becomes greater than or equal to a predetermined seventh value in the fourth control state or in a case in which a value related to the heart rate of the rider becomes less than or equal to a predetermined eighth value in the fourth control state.

17. The human-powered vehicle control device according to claim 1, further comprising
a first detector that outputs a signal corresponding to an operation of an operation unit used to operate the transmission, the electronic controller being configured to change a control state of the motor in accordance with the output of the first detector.

18. The human-powered vehicle control device according to claim 1, wherein
the transmission is configured to be driven by an electric actuator, and
the electronic controller is configured to control the electric actuator.

* * * * *